(12) United States Patent
Patel et al.

(10) Patent No.: US 9,345,510 B2
(45) Date of Patent: May 24, 2016

(54) ATHERECTOMY CATHETERS WITH LONGITUDINALLY DISPLACEABLE DRIVE SHAFTS

(75) Inventors: Himanshu N. Patel, San Jose, CA (US); John B. Simpson, Woodside, CA (US); Charles W. McNall, Salt Lake City, UT (US); Maegan K. Spencer, Emerald Hills, CA (US); Michael Zung, San Carlos, CA (US); Priyanshu Gupta, Palo Alto, CA (US)

(73) Assignee: Avinger, Inc., Redwood City, CA (US)

( * ) Notice: Subject to any disclaimer, the term of this patent is extended or adjusted under 35 U.S.C. 154(b) by 0 days.

(21) Appl. No.: 13/175,232

(22) Filed: Jul. 1, 2011

(65) Prior Publication Data
US 2012/0046679 A1 Feb. 23, 2012

Related U.S. Application Data

(60) Provisional application No. 61/360,886, filed on Jul. 1, 2010, provisional application No. 61/468,396, filed on Mar. 28, 2011, provisional application No. 61/492,693, filed on Jun. 2, 2011.

(51) Int. Cl.
A61B 17/22 (2006.01)
A61B 17/3207 (2006.01)
(Continued)

(52) U.S. Cl.
CPC ..... A61B 17/320758 (2013.01); A61B 1/00179 (2013.01); A61B 1/00183 (2013.01); A61B 1/3137 (2013.01); A61B 17/320725 (2013.01); *A61B 1/00165* (2013.01); *A61B 5/0066* (2013.01); *A61B 2090/3735* (2016.02)

(58) Field of Classification Search
CPC ............ A61B 17/320725; A61B 17/32075; A61B 17/320758; A61B 19/5225
USPC ................... 606/159, 167, 179, 180
See application file for complete search history.

(56) References Cited

U.S. PATENT DOCUMENTS 4,178,935 A 12/1979 Gekhaman et al.
4,552,554 A 11/1985 Gould et al.
(Continued)

FOREIGN PATENT DOCUMENTS

CN 1875242 A 12/2006
CN 1947652 A 4/2007
(Continued)

OTHER PUBLICATIONS

Patel et al.; U.S. Appl. No. 13/752,325 entitled "Catheter system and method for boring through blocked vascular passages," filed Jan. 28, 2013.
(Continued)

*Primary Examiner* — Corrinne McDermott
*Assistant Examiner* — Sarah Simpson
(74) *Attorney, Agent, or Firm* — Shay Glenn LLP

(57) ABSTRACT

Described herein are atherectomy catheters, systems and methods that include longitudinally displaceable drive shafts that drive actuation of one or more cutters at the distal end of the catheter. The catheters described herein may include one or more imaging sensors for imaging before, during or after cutting tissue. In some variations the imaging sensor may be rotated around the perimeter of the catheter independently of the rotation of the cutter. Also describe herein are imaging catheters that may be used without cutters.

11 Claims, 27 Drawing Sheets

(51) Int. Cl.
  *A61B 1/313* (2006.01)
  *A61B 1/00* (2006.01)
  *A61B 5/00* (2006.01)

(56) References Cited

U.S. PATENT DOCUMENTS

| | | | |
|---|---|---|---|
| 4,621,353 A | 11/1986 | Hazel et al. | |
| 4,639,091 A | 1/1987 | Huignard et al. | |
| 4,654,024 A | 3/1987 | Crittenden et al. | |
| 4,686,982 A | 8/1987 | Nash | |
| 4,771,774 A | 9/1988 | Simpson et al. | |
| 4,841,977 A | 6/1989 | Griffith et al. | |
| 4,926,858 A | 5/1990 | Gifford, III et al. | |
| 5,000,185 A | 3/1991 | Yock | |
| 5,041,082 A | 8/1991 | Shiber | |
| 5,047,040 A | 9/1991 | Simpson et al. | |
| 5,085,662 A | 2/1992 | Willard | |
| 5,099,850 A | 3/1992 | Matsui et al. | |
| 5,178,153 A | 1/1993 | Einzig | |
| 5,182,291 A | 1/1993 | Gubin et al. | |
| 5,190,050 A | 3/1993 | Nitzsche | |
| 5,192,291 A | 3/1993 | Pannek, Jr. | |
| 5,312,415 A | 5/1994 | Palermo | |
| 5,312,425 A | 5/1994 | Evans et al. | |
| 5,321,501 A | 6/1994 | Swanson et al. | |
| 5,333,142 A | 7/1994 | Scheps | |
| 5,358,472 A | 10/1994 | Vance et al. | |
| 5,383,460 A | 1/1995 | Jang et al. | |
| 5,383,467 A | 1/1995 | Auer et al. | |
| 5,429,136 A | 7/1995 | Milo et al. | |
| 5,431,673 A | 7/1995 | Summers et al. | |
| 5,459,570 A | 10/1995 | Swanson et al. | |
| 5,465,147 A | 11/1995 | Swanson | |
| 5,556,405 A | 9/1996 | Lary | |
| 5,632,754 A | 5/1997 | Farley et al. | |
| 5,632,755 A | 5/1997 | Nordgren et al. | |
| 5,674,232 A | 10/1997 | Halliburton | |
| 5,681,336 A | 10/1997 | Clement et al. | |
| 5,690,634 A | 11/1997 | Muller et al. | |
| 5,722,403 A | 3/1998 | McGee et al. | |
| 5,795,295 A | 8/1998 | Hellmuth et al. | |
| 5,807,339 A | 9/1998 | Bostrom et al. | |
| 5,830,145 A | 11/1998 | Tenhoff | |
| 5,843,050 A | 12/1998 | Jones et al. | |
| 5,868,778 A | 2/1999 | Gershony et al. | |
| 5,872,879 A | 2/1999 | Hamm | |
| 5,904,651 A | 5/1999 | Swanson et al. | |
| 5,907,425 A | 5/1999 | Dickensheets et al. | |
| 5,935,075 A | 8/1999 | Casscells et al. | |
| 5,938,602 A | 8/1999 | Lloyd | |
| 5,951,482 A | 9/1999 | Winston et al. | |
| 5,951,581 A | 9/1999 | Saadat et al. | |
| 5,951,583 A | 9/1999 | Jensen et al. | |
| 5,956,355 A | 9/1999 | Swanson et al. | |
| 5,957,952 A | 9/1999 | Gershony et al. | |
| 5,987,995 A | 11/1999 | Sawatari et al. | |
| 5,997,558 A | 12/1999 | Nash | |
| 6,001,112 A | 12/1999 | Taylor | |
| 6,007,530 A | 12/1999 | Dornhofer et al. | |
| 6,010,449 A | 1/2000 | Selmon et al. | |
| 6,013,072 A | 1/2000 | Winston et al. | |
| 6,017,359 A | 1/2000 | Gershony et al. | |
| 6,027,514 A | 2/2000 | Stine et al. | |
| 6,032,673 A | 3/2000 | Savage et al. | |
| 6,048,349 A | 4/2000 | Winston et al. | |
| 6,080,170 A | 6/2000 | Nash et al. | |
| 6,106,515 A | 8/2000 | Winston et al. | |
| 6,110,164 A | 8/2000 | Vidlund | |
| 6,120,515 A | 9/2000 | Rogers et al. | |
| 6,120,516 A | 9/2000 | Selmon et al. | |
| 6,134,002 A | 10/2000 | Stimson et al. | |
| 6,134,003 A | 10/2000 | Tearney et al. | |
| 6,152,938 A | 11/2000 | Curry | |
| 6,152,951 A | 11/2000 | Hashimoto et al. | |
| 6,160,826 A | 12/2000 | Swanson et al. | |
| 6,175,669 B1 | 1/2001 | Colston et al. | |
| 6,176,871 B1 | 1/2001 | Pathak et al. | |
| 6,183,432 B1 | 2/2001 | Milo | |
| 6,193,676 B1 | 2/2001 | Winston et al. | |
| 6,206,898 B1 | 3/2001 | Honeycutt et al. | |
| 6,228,076 B1 | 5/2001 | Winston et al. | |
| 6,241,744 B1 | 6/2001 | Imran et al. | |
| 6,283,957 B1 | 9/2001 | Hashimoto et al. | |
| 6,290,668 B1 | 9/2001 | Gregory et al. | |
| 6,294,775 B1 | 9/2001 | Seibel et al. | |
| 6,299,622 B1 | 10/2001 | Snow et al. | |
| 6,307,985 B1 | 10/2001 | Murakami et al. | |
| 6,402,719 B1 | 6/2002 | Ponzi et al. | |
| 6,445,939 B1 | 9/2002 | Swanson et al. | |
| 6,445,944 B1 | 9/2002 | Ostrovsky | |
| 6,447,525 B2 | 9/2002 | Follmer et al. | |
| 6,451,036 B1 | 9/2002 | Heitzmann et al. | |
| 6,454,779 B1 | 9/2002 | Taylor | |
| 6,482,217 B1 | 11/2002 | Pintor et al. | |
| 6,485,413 B1 | 11/2002 | Boppart et al. | |
| 6,497,649 B2 | 12/2002 | Parker et al. | |
| 6,501,551 B1 | 12/2002 | Tearney et al. | |
| 6,503,261 B1 | 1/2003 | Bruneau et al. | |
| 6,511,458 B2 | 1/2003 | Milo et al. | |
| 6,517,528 B1 | 2/2003 | Pantages et al. | |
| 6,542,665 B2 | 4/2003 | Reed et al. | |
| 6,546,272 B1 | 4/2003 | MacKinnon et al. | |
| 6,551,302 B1 | 4/2003 | Rosinko et al. | |
| 6,563,105 B2 | 5/2003 | Seibel et al. | |
| 6,564,087 B1 | 5/2003 | Pitris et al. | |
| 6,565,588 B1 | 5/2003 | Clement et al. | |
| 6,572,643 B1 | 6/2003 | Gharibadeh | |
| 6,575,995 B1 | 6/2003 | Huter et al. | |
| 6,579,298 B1 | 6/2003 | Bruneau et al. | |
| 6,615,071 B1 | 9/2003 | Casscells, III et al. | |
| 6,623,496 B2 | 9/2003 | Snow et al. | |
| 6,638,233 B2 | 10/2003 | Corvi et al. | |
| 6,645,217 B1 | 11/2003 | MacKinnon et al. | |
| 6,666,874 B2 | 12/2003 | Heitzmann et al. | |
| 6,687,010 B1 | 2/2004 | Horii | |
| 6,728,571 B1 | 4/2004 | Barbato | |
| D489,973 S | 5/2004 | Root et al. | |
| 6,730,063 B2 | 5/2004 | Delaney et al. | |
| 6,758,854 B1 | 7/2004 | Butler et al. | |
| 6,760,112 B2 | 7/2004 | Reed et al. | |
| 6,800,085 B2 | 10/2004 | Selmon et al. | |
| 6,818,001 B2 | 11/2004 | Wulfman et al. | |
| 6,824,550 B1 | 11/2004 | Noriega et al. | |
| 6,830,577 B2 | 12/2004 | Nash et al. | |
| 6,845,190 B1 | 1/2005 | Smithwick et al. | |
| 6,852,109 B2 | 2/2005 | Winston et al. | |
| 6,853,457 B2 | 2/2005 | Bjarklev et al. | |
| 6,856,712 B2 | 2/2005 | Fauver et al. | |
| 6,867,753 B2 | 3/2005 | Chinthammit et al. | |
| 6,879,851 B2 | 4/2005 | McNamara et al. | |
| 6,947,787 B2 | 9/2005 | Webler | |
| 6,961,123 B1 | 11/2005 | Wang et al. | |
| 6,970,732 B2 | 11/2005 | Winston et al. | |
| 6,975,898 B2 | 12/2005 | Seibel | |
| 7,068,878 B2 | 6/2006 | Crossman-Bosworth et al. | |
| 7,074,231 B2 | 7/2006 | Jang | |
| 7,126,693 B2 | 10/2006 | Everett et al. | |
| 7,172,610 B2 | 2/2007 | Heitzmann et al. | |
| 7,242,480 B2 | 7/2007 | Alphonse | |
| 7,261,687 B2 | 8/2007 | Yang | |
| 7,288,087 B2 | 10/2007 | Winston et al. | |
| 7,291,146 B2 | 11/2007 | Steinke et al. | |
| 7,297,131 B2 | 11/2007 | Nita | |
| 7,311,723 B2 | 12/2007 | Seibel et al. | |
| 7,344,546 B2 * | 3/2008 | Wulfman et al. | 606/159 |
| 7,366,376 B2 | 4/2008 | Shishkov et al. | |
| 7,382,949 B2 | 6/2008 | Bouma et al. | |
| 7,426,036 B2 | 9/2008 | Feldchtein et al. | |
| 7,428,001 B2 | 9/2008 | Schowengerdt et al. | |
| 7,428,053 B2 | 9/2008 | Feldchtein et al. | |
| 7,455,649 B2 | 11/2008 | Root et al. | |
| 7,474,407 B2 | 1/2009 | Gutin | |
| 7,485,127 B2 | 2/2009 | Nistal | |
| 7,488,340 B2 | 2/2009 | Kauphusman et al. | |

(56) References Cited

U.S. PATENT DOCUMENTS

| | | |
|---|---|---|
| 7,530,948 B2 | 5/2009 | Seibel et al. |
| 7,530,976 B2 | 5/2009 | MacMahon et al. |
| 7,538,859 B2 | 5/2009 | Tearney et al. |
| 7,538,886 B2 | 5/2009 | Feldchtein |
| 7,539,362 B2 | 5/2009 | Teramura |
| 7,542,145 B2 | 6/2009 | Toida et al. |
| 7,544,162 B2 | 6/2009 | Ohkubo |
| 7,545,504 B2 | 6/2009 | Buckland et al. |
| 7,555,333 B2 | 6/2009 | Wang et al. |
| 7,577,471 B2 | 8/2009 | Camus et al. |
| 7,583,872 B2 | 9/2009 | Seibel et al. |
| 7,616,986 B2 | 11/2009 | Seibel et al. |
| 7,637,885 B2 | 12/2009 | Maschke |
| 7,674,253 B2 | 3/2010 | Fisher et al. |
| 7,706,863 B2 | 4/2010 | Imanishi et al. |
| 7,728,985 B2 | 6/2010 | Feldchtein et al. |
| 7,734,332 B2 | 6/2010 | Sher |
| 7,738,945 B2 | 6/2010 | Fauver et al. |
| 7,753,852 B2 | 7/2010 | Maschke |
| 7,771,425 B2 | 8/2010 | Dycus et al. |
| 7,785,286 B2 | 8/2010 | Magnin et al. |
| 7,813,609 B2 | 10/2010 | Petersen et al. |
| 7,821,643 B2 | 10/2010 | Amazeen et al. |
| 7,824,089 B2 | 11/2010 | Charles |
| 7,840,283 B1 | 11/2010 | Bush et al. |
| 7,944,568 B2 | 5/2011 | Teramura et al. |
| 7,952,718 B2 | 5/2011 | Li et al. |
| 7,972,299 B2 | 7/2011 | Carter et al. |
| 8,059,274 B2 | 11/2011 | Splinter |
| 8,062,316 B2 | 11/2011 | Patel et al. |
| 8,313,493 B2 | 11/2012 | Fisher |
| 8,548,603 B2 | 10/2013 | Swoyer et al. |
| 2001/0020126 A1 | 9/2001 | Swanson et al. |
| 2002/0019644 A1 | 2/2002 | Hastings et al. |
| 2002/0082626 A1 | 6/2002 | Donohoe et al. |
| 2002/0111548 A1 | 8/2002 | Swanson et al. |
| 2002/0115931 A1 | 8/2002 | Strauss et al. |
| 2002/0158547 A1 | 10/2002 | Wood |
| 2003/0028100 A1 | 2/2003 | Tearney et al. |
| 2003/0032880 A1 | 2/2003 | Moore |
| 2003/0045835 A1 | 3/2003 | Anderson et al. |
| 2003/0095248 A1 | 5/2003 | Frot |
| 2003/0097044 A1 | 5/2003 | Rovegno |
| 2003/0120295 A1 | 6/2003 | Simpson et al. |
| 2003/0125756 A1* | 7/2003 | Shturman et al. ............. 606/159 |
| 2003/0125757 A1 | 7/2003 | Patel et al. |
| 2003/0125758 A1 | 7/2003 | Simpson et al. |
| 2004/0002650 A1 | 1/2004 | Mandrusov et al. |
| 2004/0039371 A1 | 2/2004 | Tockman et al. |
| 2004/0057667 A1 | 3/2004 | Yamada et al. |
| 2004/0082850 A1 | 4/2004 | Bonner et al. |
| 2004/0092915 A1 | 5/2004 | Levatter |
| 2004/0147934 A1 | 7/2004 | Kiester |
| 2004/0167553 A1* | 8/2004 | Simpson et al. ............. 606/159 |
| 2004/0167554 A1 | 8/2004 | Simpson et al. |
| 2004/0181249 A1 | 9/2004 | Torrance et al. |
| 2004/0186368 A1 | 9/2004 | Ramzipoor et al. |
| 2004/0202418 A1 | 10/2004 | Ghiron et al. |
| 2004/0220519 A1 | 11/2004 | Wulfman et al. |
| 2004/0230212 A1 | 11/2004 | Wulfman |
| 2004/0230213 A1 | 11/2004 | Wulfman et al. |
| 2004/0236312 A1 | 11/2004 | Nistal et al. |
| 2004/0243162 A1 | 12/2004 | Wulfman et al. |
| 2004/0254599 A1 | 12/2004 | Lipoma et al. |
| 2004/0260236 A1 | 12/2004 | Manning et al. |
| 2005/0020925 A1 | 1/2005 | Kleen et al. |
| 2005/0043614 A1 | 2/2005 | Huizenga et al. |
| 2005/0054947 A1 | 3/2005 | Goldenberg |
| 2005/0085708 A1 | 4/2005 | Fauver et al. |
| 2005/0085721 A1 | 4/2005 | Fauver et al. |
| 2005/0105097 A1 | 5/2005 | Fang-Yen et al. |
| 2005/0141843 A1 | 6/2005 | Warden et al. |
| 2005/0154407 A1 | 7/2005 | Simpson |
| 2005/0159712 A1 | 7/2005 | Andersen |
| 2005/0159731 A1 | 7/2005 | Lee |
| 2005/0177068 A1 | 8/2005 | Simpson |
| 2005/0182295 A1 | 8/2005 | Soper et al. |
| 2005/0187571 A1 | 8/2005 | Maschke |
| 2005/0192496 A1 | 9/2005 | Maschke |
| 2005/0201662 A1 | 9/2005 | Petersen et al. |
| 2005/0222519 A1 | 10/2005 | Simpson |
| 2005/0222663 A1 | 10/2005 | Simpson et al. |
| 2005/0251116 A1 | 11/2005 | Steinke et al. |
| 2006/0015126 A1* | 1/2006 | Sher ............................. 606/159 |
| 2006/0032508 A1 | 2/2006 | Simpson |
| 2006/0046235 A1 | 3/2006 | Alexander |
| 2006/0064009 A1 | 3/2006 | Webler et al. |
| 2006/0084911 A1 | 4/2006 | Belef et al. |
| 2006/0109478 A1 | 5/2006 | Tearney et al. |
| 2006/0135870 A1* | 6/2006 | Webler ......................... 600/431 |
| 2006/0173475 A1 | 8/2006 | Lafontaine et al. |
| 2006/0229646 A1 | 10/2006 | Sparks |
| 2006/0229659 A1 | 10/2006 | Gifford et al. |
| 2006/0235366 A1 | 10/2006 | Simpson |
| 2006/0236019 A1 | 10/2006 | Soito et al. |
| 2006/0239982 A1 | 10/2006 | Simpson |
| 2006/0241503 A1 | 10/2006 | Schmitt et al. |
| 2006/0244973 A1 | 11/2006 | Yun et al. |
| 2006/0252993 A1 | 11/2006 | Freed et al. |
| 2006/0264741 A1 | 11/2006 | Prince |
| 2007/0010840 A1 | 1/2007 | Rosenthal et al. |
| 2007/0015969 A1 | 1/2007 | Feldman et al. |
| 2007/0015979 A1 | 1/2007 | Redel |
| 2007/0035855 A1 | 2/2007 | Dickensheets |
| 2007/0038061 A1 | 2/2007 | Huennekens et al. |
| 2007/0038173 A1 | 2/2007 | Simpson |
| 2007/0078469 A1 | 4/2007 | Soito et al. |
| 2007/0081166 A1 | 4/2007 | Brown et al. |
| 2007/0106155 A1 | 5/2007 | Goodnow et al. |
| 2007/0135712 A1 | 6/2007 | Maschke |
| 2007/0196926 A1 | 8/2007 | Soito et al. |
| 2007/0255252 A1 | 11/2007 | Mehta |
| 2007/0270647 A1 | 11/2007 | Nahen et al. |
| 2007/0276419 A1 | 11/2007 | Rosenthal |
| 2007/0288036 A1 | 12/2007 | Seshadri |
| 2007/0299309 A1 | 12/2007 | Seibel et al. |
| 2008/0004643 A1 | 1/2008 | To et al. |
| 2008/0004644 A1 | 1/2008 | To et al. |
| 2008/0004645 A1 | 1/2008 | To et al. |
| 2008/0004646 A1 | 1/2008 | To et al. |
| 2008/0015491 A1 | 1/2008 | Bei et al. |
| 2008/0027334 A1 | 1/2008 | Langston |
| 2008/0033396 A1 | 2/2008 | Danek et al. |
| 2008/0045986 A1 | 2/2008 | To et al. |
| 2008/0049234 A1 | 2/2008 | Seitz |
| 2008/0058629 A1 | 3/2008 | Seibel et al. |
| 2008/0065124 A1 | 3/2008 | Olson |
| 2008/0065125 A1 | 3/2008 | Olson |
| 2008/0065205 A1 | 3/2008 | Nguyen et al. |
| 2008/0103439 A1 | 5/2008 | Torrance et al. |
| 2008/0103446 A1 | 5/2008 | Torrance et al. |
| 2008/0103516 A1 | 5/2008 | Wulfman et al. |
| 2008/0139897 A1 | 6/2008 | Ainsworth et al. |
| 2008/0147000 A1 | 6/2008 | Seibel et al. |
| 2008/0154293 A1 | 6/2008 | Taylor et al. |
| 2008/0177138 A1 | 7/2008 | Courtney et al. |
| 2008/0186501 A1 | 8/2008 | Xie |
| 2008/0221388 A1 | 9/2008 | Seibel et al. |
| 2008/0228033 A1 | 9/2008 | Tumlinson et al. |
| 2008/0243030 A1 | 10/2008 | Seibel et al. |
| 2008/0243031 A1 | 10/2008 | Seibel et al. |
| 2008/0262312 A1 | 10/2008 | Carroll et al. |
| 2008/0275485 A1 | 11/2008 | Bonnette et al. |
| 2009/0018565 A1 | 1/2009 | To et al. |
| 2009/0018566 A1 | 1/2009 | Escudero et al. |
| 2009/0018567 A1 | 1/2009 | Escudero et al. |
| 2009/0024084 A1 | 1/2009 | Khosla et al. |
| 2009/0024085 A1 | 1/2009 | To et al. |
| 2009/0024191 A1 | 1/2009 | Seibel et al. |
| 2009/0028407 A1 | 1/2009 | Seibel et al. |
| 2009/0073444 A1 | 3/2009 | Wang |
| 2009/0093764 A1 | 4/2009 | Pfeffer et al. |
| 2009/0099641 A1 | 4/2009 | Wu et al. |
| 2009/0135280 A1 | 5/2009 | Johnston et al. |

(56) References Cited

U.S. PATENT DOCUMENTS

| | | | |
|---|---|---|---|
| 2009/0137893 A1 | 5/2009 | Seibel et al. | |
| 2009/0152664 A1 | 6/2009 | Tian et al. | |
| 2009/0185135 A1 | 7/2009 | Volk | |
| 2009/0198125 A1 | 8/2009 | Nakabayashi et al. | |
| 2009/0208143 A1 | 8/2009 | Yoon et al. | |
| 2009/0216180 A1 | 8/2009 | Lee et al. | |
| 2009/0221904 A1 | 9/2009 | Shealy et al. | |
| 2009/0221920 A1 | 9/2009 | Boppart et al. | |
| 2009/0235396 A1 | 9/2009 | Wang et al. | |
| 2009/0244485 A1 | 10/2009 | Walsh et al. | |
| 2009/0264826 A1 | 10/2009 | Thompson | |
| 2009/0284749 A1 | 11/2009 | Johnson et al. | |
| 2009/0292199 A1 | 11/2009 | Bielewicz et al. | |
| 2009/0306520 A1 | 12/2009 | Schmitt et al. | |
| 2009/0316116 A1 | 12/2009 | Melville et al. | |
| 2009/0318862 A1 | 12/2009 | Ali et al. | |
| 2010/0049225 A1 | 2/2010 | To et al. | |
| 2010/0125253 A1 | 5/2010 | Olson | |
| 2010/0130996 A1 | 5/2010 | Doud et al. | |
| 2010/0241147 A1* | 9/2010 | Maschke | 606/159 |
| 2010/0253949 A1 | 10/2010 | Adler et al. | |
| 2010/0274270 A1 | 10/2010 | Patel et al. | |
| 2010/0280534 A1* | 11/2010 | Sher | 606/159 |
| 2010/0292539 A1 | 11/2010 | Lankenau et al. | |
| 2010/0292721 A1 | 11/2010 | Moberg | |
| 2010/0305452 A1 | 12/2010 | Black et al. | |
| 2010/0312263 A1 | 12/2010 | Moberg et al. | |
| 2010/0317973 A1 | 12/2010 | Nita | |
| 2010/0324472 A1 | 12/2010 | Wulfman | |
| 2011/0004107 A1 | 1/2011 | Rosenthal et al. | |
| 2011/0021926 A1 | 1/2011 | Spencer et al. | |
| 2011/0040238 A1 | 2/2011 | Wulfman et al. | |
| 2011/0106004 A1 | 5/2011 | Eubanks et al. | |
| 2011/0118660 A1 | 5/2011 | Torrance et al. | |
| 2011/0130777 A1 | 6/2011 | Zhang et al. | |
| 2011/0144673 A1 | 6/2011 | Zhang et al. | |
| 2011/0201924 A1 | 8/2011 | Tearney et al. | |
| 2011/0263936 A1 | 10/2011 | He et al. | |
| 2011/0301625 A1 | 12/2011 | Mauch et al. | |
| 2012/0004506 A1 | 1/2012 | Tearney et al. | |
| 2012/0041307 A1 | 2/2012 | Patel et al. | |
| 2012/0123352 A1 | 5/2012 | Fruland et al. | |
| 2012/0238869 A1 | 9/2012 | Schmitt et al. | |
| 2012/0289971 A1 | 11/2012 | Segermark et al. | |
| 2013/0289392 A1 | 10/2013 | Patel et al. | |
| 2013/0296695 A1 | 11/2013 | Spencer et al. | |
| 2014/0213893 A1 | 7/2014 | Simpson et al. | |
| 2015/0208922 A1 | 7/2015 | Simpson et al. | |
| 2016/0008025 A1 | 1/2016 | Gupta et al. | |
| 2016/0029902 A1 | 2/2016 | Smith et al. | |
| 2016/0038030 A1 | 2/2016 | Smith et al. | |

FOREIGN PATENT DOCUMENTS

| | | |
|---|---|---|
| CN | 101601581 A | 12/2009 |
| DE | 202006018883.5 U1 | 2/2007 |
| EP | 0347098 A2 | 12/1989 |
| EP | 0808638 A1 | 11/1997 |
| EP | 1859732 A1 | 11/2007 |
| EP | 2353526 B1 | 9/2013 |
| JP | 2002-214127 A | 7/2002 |
| JP | 2004-509695 A | 4/2004 |
| JP | 2004-516073 | 6/2004 |
| JP | 2005-114473 A | 4/2005 |
| JP | 2005-249704 A | 9/2005 |
| JP | 2008-175698 A | 7/2006 |
| JP | 2006-288775 A | 10/2006 |
| JP | 2006-313158 A | 11/2006 |
| JP | 2006-526790 | 11/2006 |
| JP | 2006-326157 A | 12/2006 |
| JP | 2007-225349 A | 9/2007 |
| JP | 2008-023627 | 2/2008 |
| JP | 2008-128708 A | 6/2008 |
| JP | 2008-145376 A | 6/2008 |
| JP | 2008-183208 A | 8/2008 |
| JP | 2008-253492 A | 10/2008 |
| JP | 2009-14751 A | 1/2009 |
| JP | 2009-509690 A | 3/2009 |
| JP | 2009-78150 A | 4/2009 |
| KR | 2007/0047221 | 5/2007 |
| RU | 2185859 C2 | 7/2002 |
| RU | 2218191 C2 | 12/2003 |
| WO | WO 91/17698 A1 | 11/1991 |
| WO | WO 99/23958 A1 | 5/1999 |
| WO | WO 00/54659 A1 | 9/2000 |
| WO | WO 01/76680 A1 | 10/2001 |
| WO | WO 2006/133030 A2 | 12/2006 |
| WO | WO 2008/029506 A | 3/2008 |
| WO | WO 2008/042987 A2 | 4/2008 |
| WO | WO 2008/086613 A1 | 7/2008 |
| WO | WO 2008/087613 A2 | 7/2008 |
| WO | WO2009/006335 A1 | 1/2009 |
| WO | WO 2009/009799 A1 | 1/2009 |
| WO | WO2009/009802 A1 | 1/2009 |
| WO | WO 2009/023635 A | 2/2009 |
| WO | WO2009/024344 A1 | 2/2009 |
| WO | WO 2009/094341 A2 | 7/2009 |
| WO | WO 2009/140617 A2 | 11/2009 |
| WO | WO2010/039464 A1 | 4/2010 |
| WO | WO2010/056771 A1 | 5/2010 |
| WO | WO 2012/061935 A1 | 5/2012 |

OTHER PUBLICATIONS

Aziz et al.; Chronic total occlusions—a stiff challenge requiring a major breakthrough: is there light at the end of the tunnel?; Heart; vol. 91; suppl. III; pp. 42-48; Jun. 2005.

Han et al.; In situ Frog Retina Imaging Using Common-Path OCT with a Gold-Coated Bare Fiber Probe; CFM6; San Jose, California; CLEO, May 4, 2008; 2 pages.

Muller et al.; Time-gated infrared fourier-domain optical coherence tomography; CFM5; San Jose, California; CLEO May 4, 2008; 2 pages.

Wang et al.; Common-path endoscopic Fourier domain OCT with a reference Michelson interferometer; Proceedings of the SPIE; vol. 7566; pp. 75660L-75660L-7; Jan. 2010.

Simpson et. al; U.S. Appl. No. 13/433,049 entitled "Occlusion-Crossing Devices, Imaging, and Atherectomy Devices," filed Mar. 28, 2012.

Spencer et al.; U.S. Appl. No. 13/654,357 entitled "Atherectomy Catheters and Non-Contact Actuation Mechanism for Catheters," filed Oct. 17, 2012.

Spencer et al.; U.S. Appl. No. 13/675,867 entitled "Occlusion-Crossing Devices, Atherectomy Devices, and Imaging," filed Nov. 13, 2012.

Emkey et al.; Analysis and evaluation of graded-index fiber-lenses; Journal of Lightwave Technology; vol. LT-5; No. 9; pp. 1156-1164; Sep. 1987.

Linares et al.; Arbitrary single-mode coupling by tapered and nontapered grin fiber lenses; Applied Optics; vol. 29; No. 28; pp. 4003-4007; Oct. 1, 1990.

Suparno et al.; Light scattering with single-mode fiber collimators; Applied Optics; vol. 33; No. 30; pp. 7200-7205; Oct. 20, 1994.

Sharma et al.; Optical coherence tomography based on an all-fiber autocorrelator using probe-end reflection as reference; CWJ13; San Francisco, California; CLEO May 16, 2004.

He et al.; U.S. Appl. No. 14/019,466 entitled "Devices and Methods for Predicting and Preventing Restenosis," filed Sep. 5, 2013.

Gonzalo et al.; Optical coherence tomography patterns of stent restenosis; Am. Heart J.; 158(2); pp. 284-293; Aug. 2009.

Tanaka et al.; Challenges on the frontier of intracoronary imaging: atherosclerotic plaque macrophage measurement by optical coherence tomography; Journal of Biomedical Optics; 15(1); pp. 011104-1-011104-8; Jan.-Feb. 2010.

Kankaria; U.S. Appl. No. 14/400,140 entitled "Optical coherence tomography with index fiber for biological imaging," filed Nov. 10, 2014.

Gupta et al.; U.S. Appl. No. 14/401,175 entitled "Atherectomy catheters with imaging," filed Nov. 14, 2014.

(56) References Cited

OTHER PUBLICATIONS

Tachibana et al.; U.S. Appl. No. 14/400,151 entitled "Atherectomy catheter drive assemblies," filed Nov. 10, 2014.
Simpson et al.; U.S. Appl. No. 14/424,266 entitled "Re-entry stylet for catheter," filed Feb. 26, 2015.
Simpson et al.; U.S. Appl. No. 14/424,277 entitled "Balloon atherectomy catheters with imaging," filed Feb. 26, 2015.
Simpson et al.; U.S. Appl. No. 14/899,877 entitled "Occusion sheath for imaging catheter," filed Dec. 18, 2015.
Simpson et al.; U.S. Appl. No. 14/899,893 entitled "Identification of elastic lamina to guide interventional therapy," filed Dec. 18, 2015.

\* cited by examiner

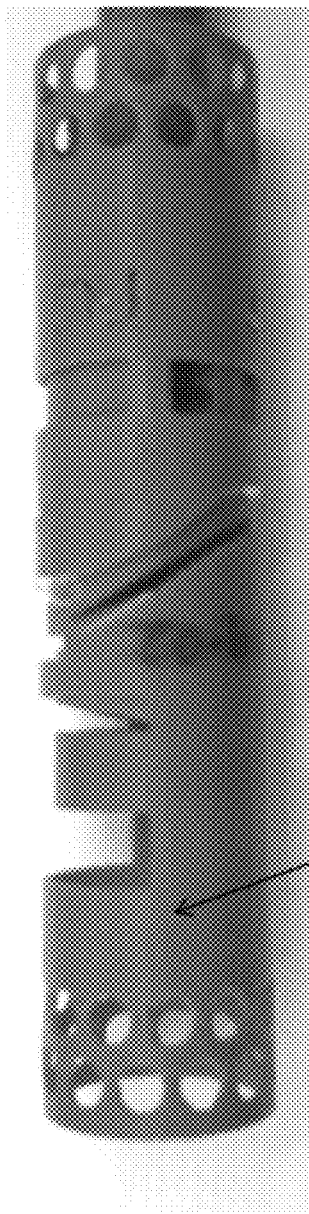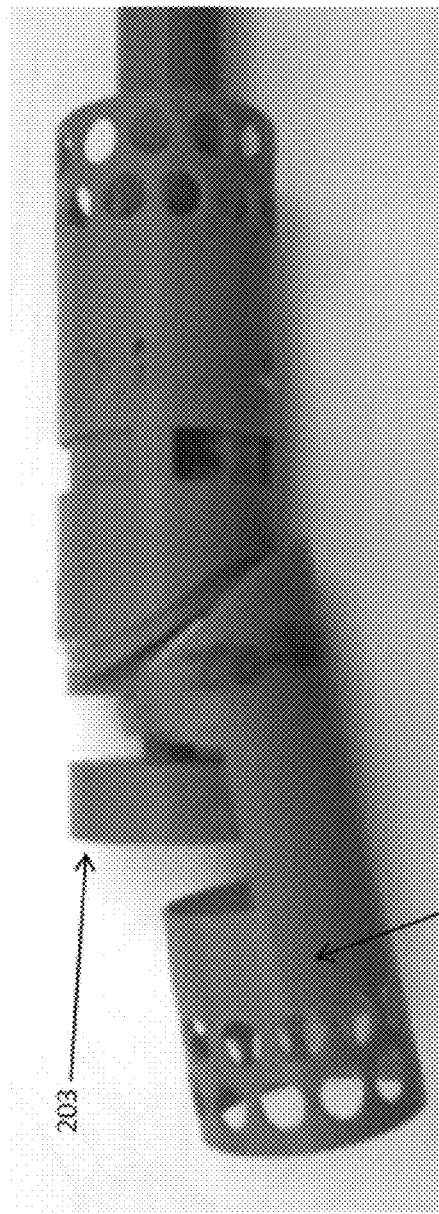

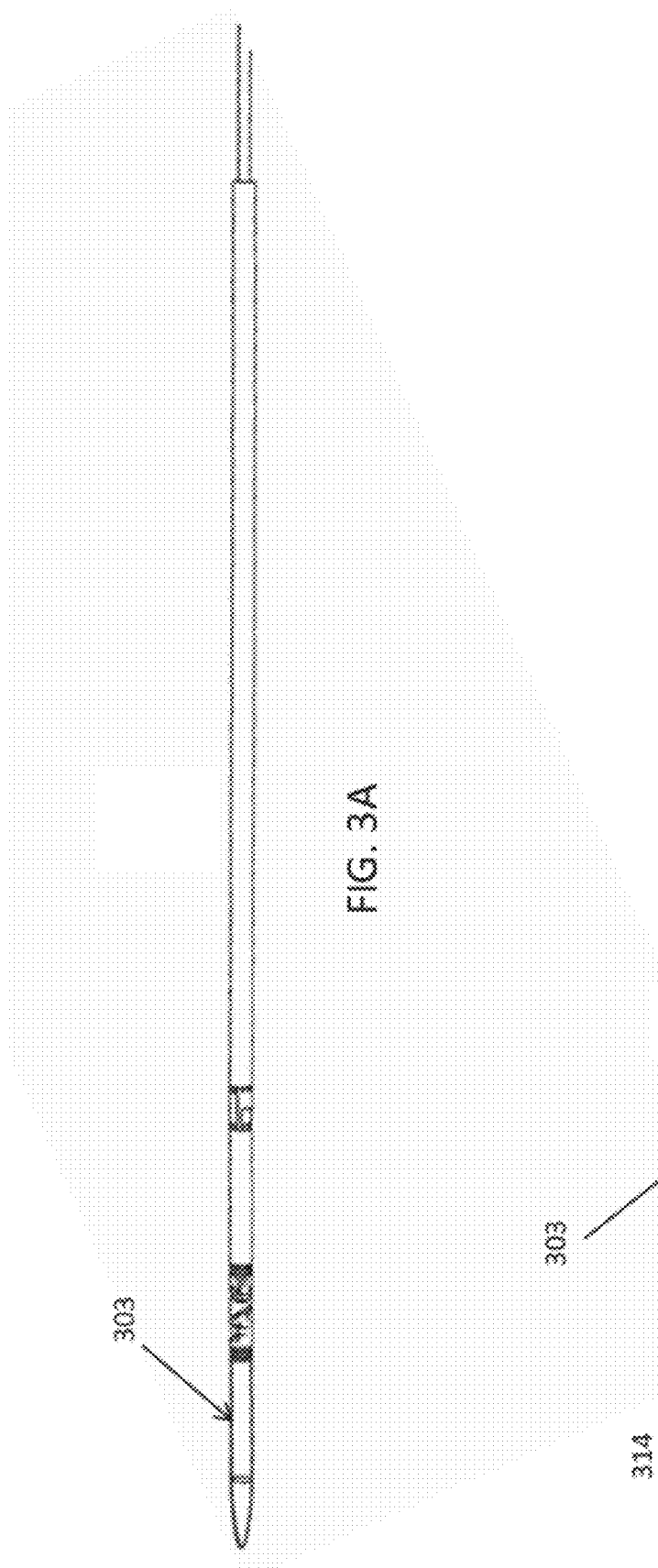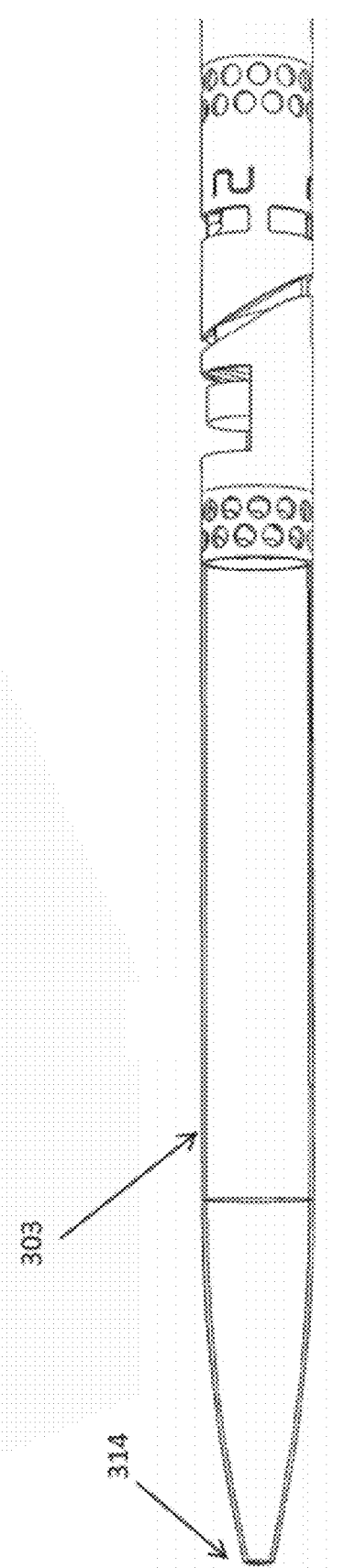

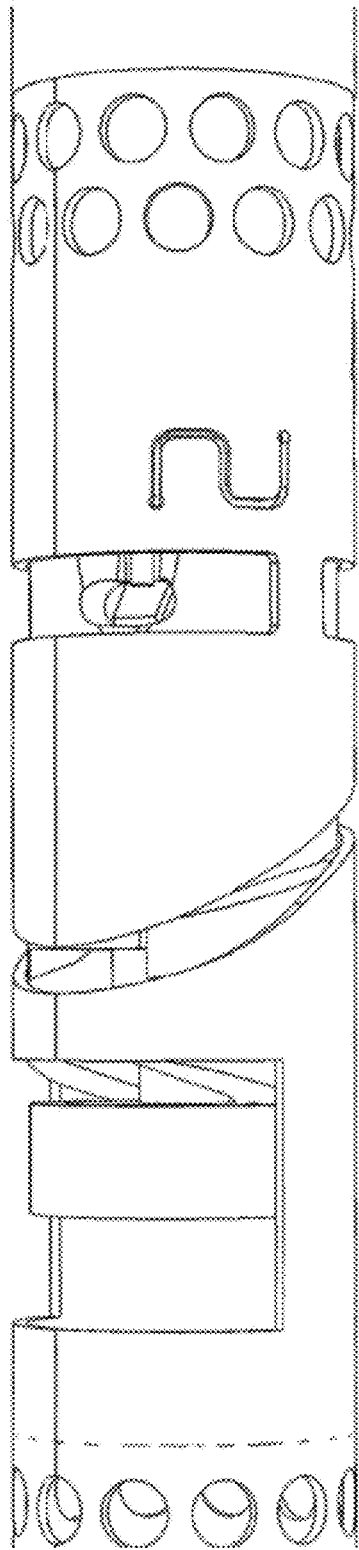
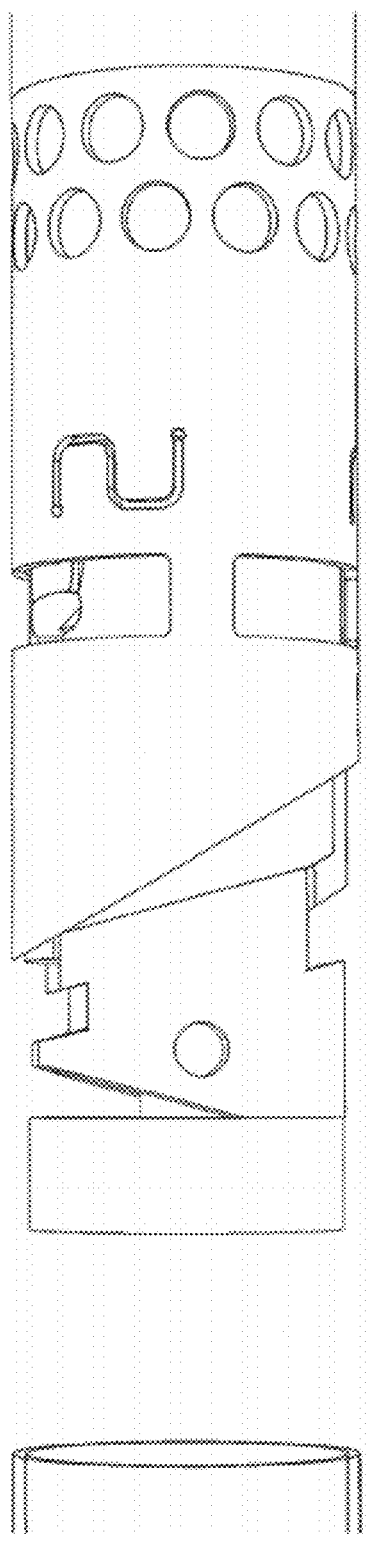
FIG. 5A
FIG. 5B

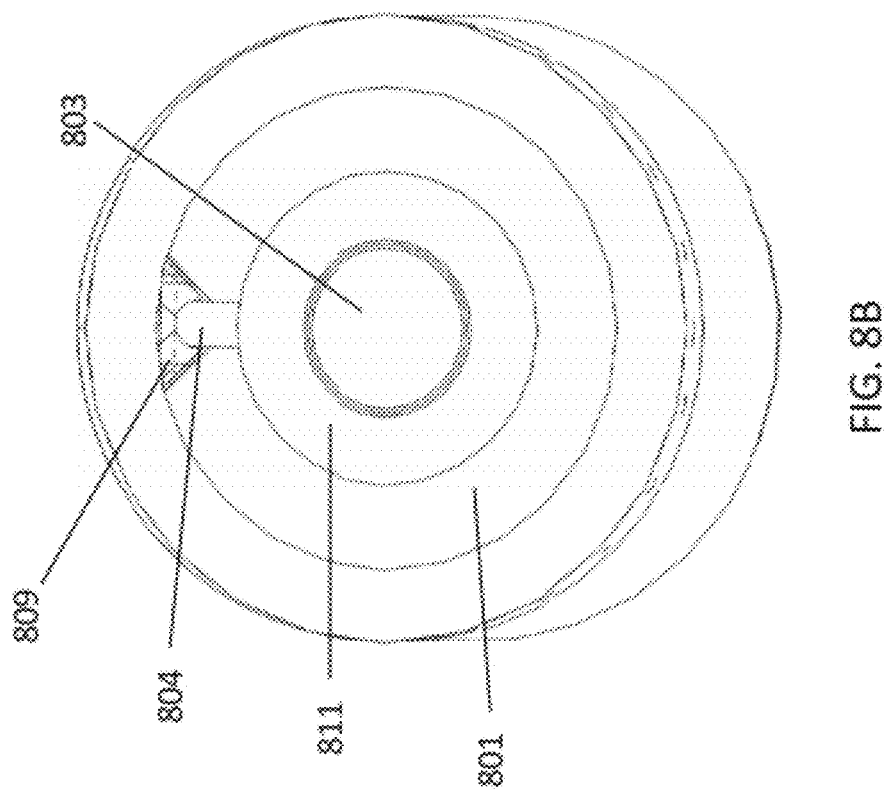
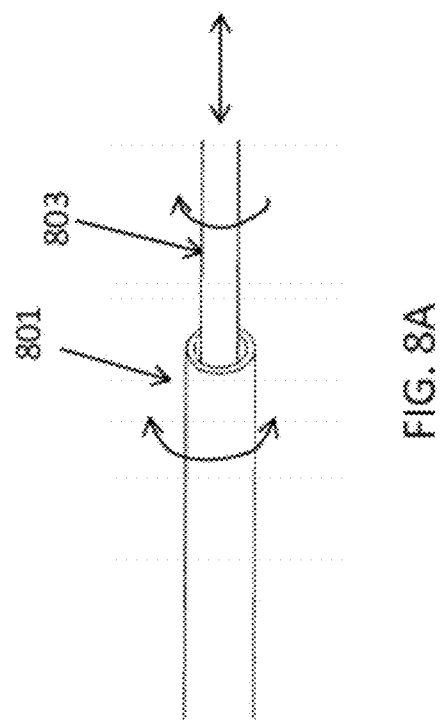
FIG. 8A
FIG. 8B

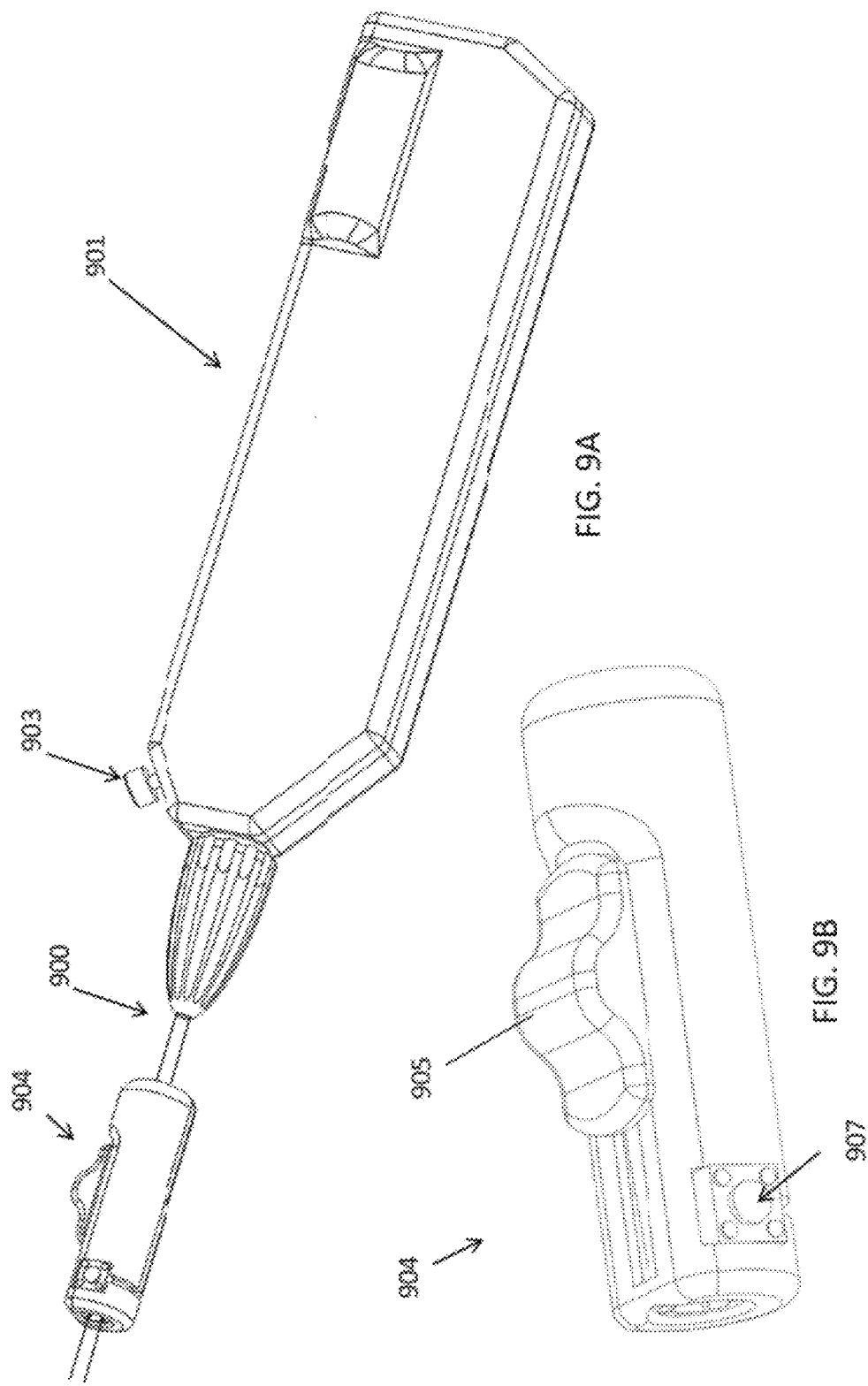

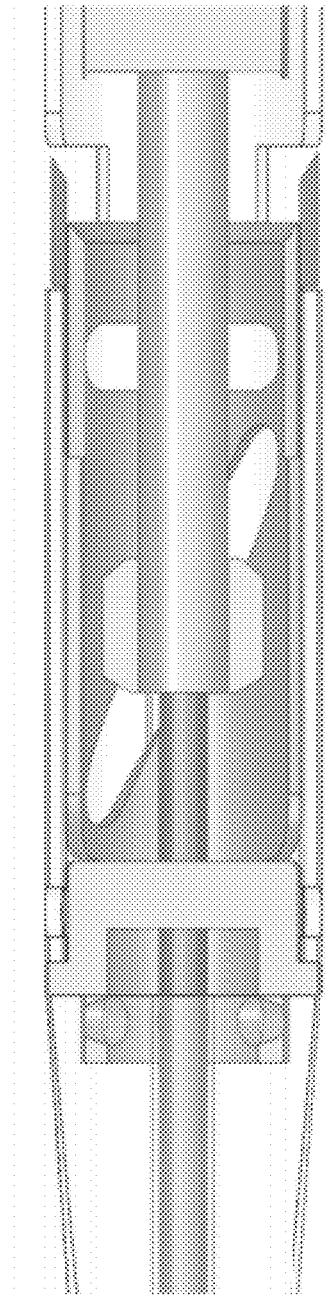

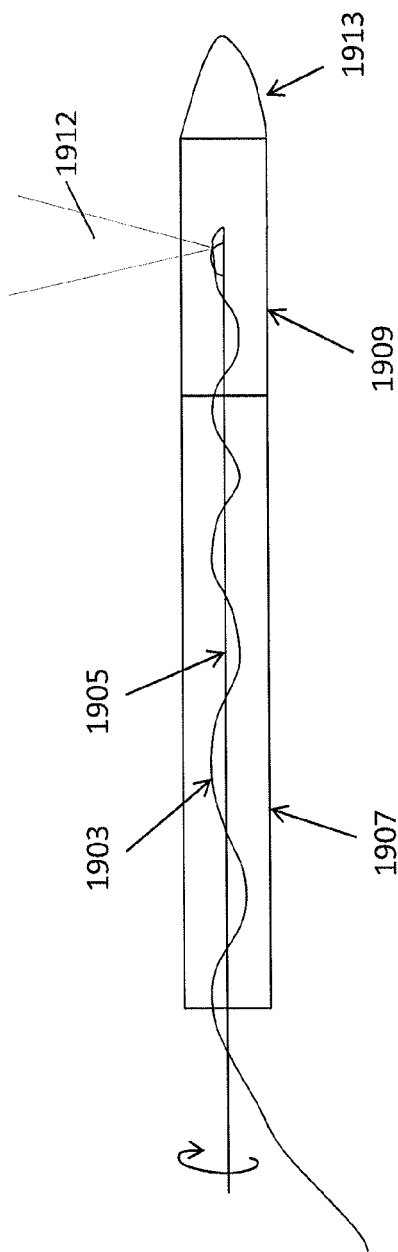
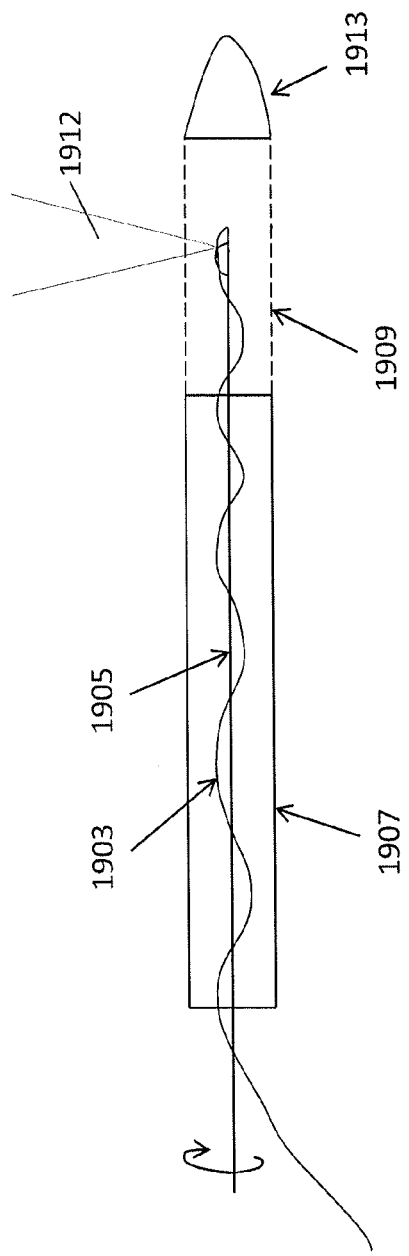
FIG. 19A
FIG. 19B

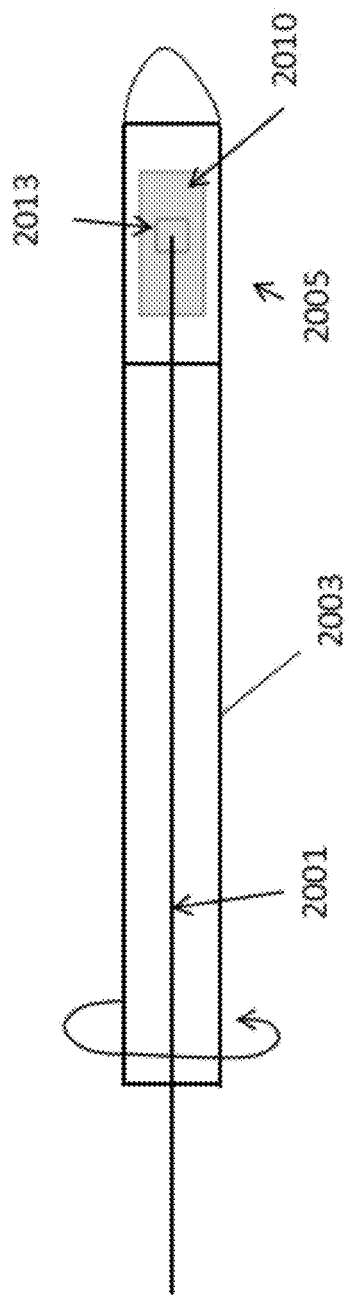

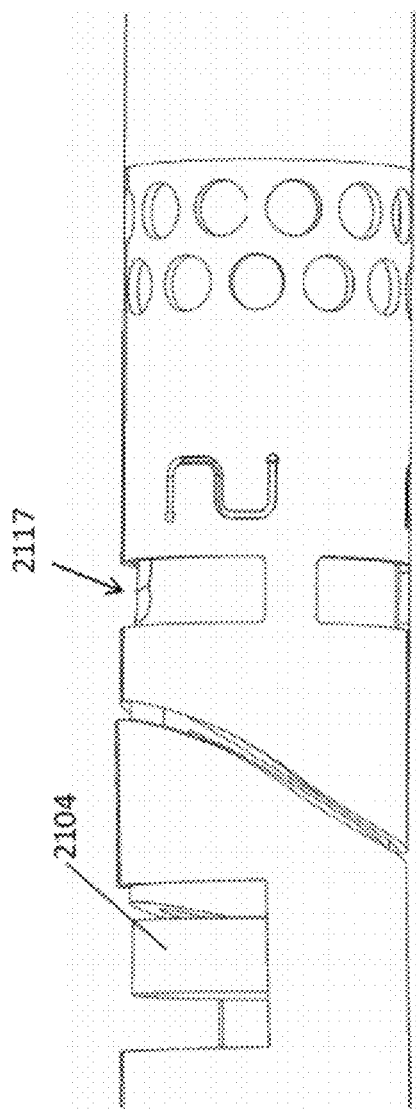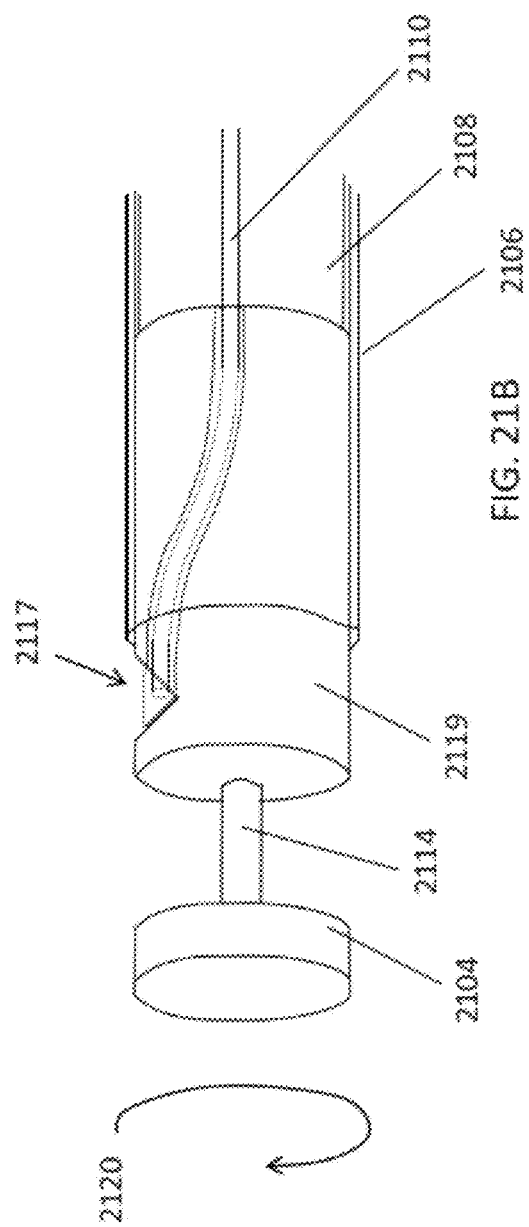
FIG. 21A
FIG. 21B

ATHERECTOMY CATHETERS WITH LONGITUDINALLY DISPLACEABLE DRIVE SHAFTS

CROSS REFERENCE TO RELATED APPLICATIONS

This patent application claims priority to U.S. Provisional Patent Application No. 61/360,886, titled "ATHERECTOMY CATHETERS WITH LONGITUDINALLY DISPLACEABLE DRIVE SHAFT," filed on Jul. 1, 2010. This patent application also claims priority to U.S. Provisional Patent Application No. 61/468,396, titled "OCCLUSION CROSSING DEVICES, IMAGING, AND ATHERECTOMY DEVICES," filed on Mar. 28, 2011. This patent application also claims priority to U.S. Provisional Patent Application No. 61/492,693, titled "ATHERECTOMY CATHETERS WITH LONGITUDINALLY DISPLACEABLE DRIVE SHAFTS" and filed on Jun. 2, 2011.

This patent application may be related to U.S. patent application Ser. No. 12/829,277, titled "ATHERECTOMY CATHETER WITH LATERALLY-DISPLACEABLE TIP," filed on Jul. 1, 2010.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD OF THE INVENTION

Described herein are atherectomy catheters with independently controlled imaging. These atherectomy catheters may include longitudinally actuated cutters, systems including such catheters and methods of using them.

BACKGROUND OF THE INVENTION

A significant body of scientific and clinical evidence supports atherectomy as a viable primary or adjunctive therapy prior to stenting for the treatment of occlusive coronary artery disease. Atherectomy offers a simple mechanical advantage over alternative therapies. By removing the majority of plaque mass (debulking) it creates a larger initial lumen and dramatically increases the compliance of the arterial wall. As a result, stent deployment is greatly enhanced.

Additionally, there are advantages related to the arterial healing response. When circumferential radial forces are applied to the vasculature, as in the case of angioplasty or stenting, the plaque mass is displaced, forcing the vessel wall to stretch dramatically. This stretch injury is a known stimulus for the cellular in-growth that leads to restenosis. By removing the disease with minimal force applied to the vessel and reducing the plaque burden prior to stent placement, large gains in lumen size can be created with decreased vessel wall injury and limited elastic recoil which have shown to translate into better acute results and lower restenosis rates.

Traditional atherectomy devices have been plagued by a number of problems, which have severely limited market adoption. These challenges include the need for large access devices, rigid distal assemblies that make control and introduction challenging, fixed cut length, unpredictable depth of cut, insufficient tissue collection and removal, and complex operation. The systems and devices described herein may overcome these hurdles and offer physicians a safe, reliable, and simple cutting system that offers the precision required in eccentric lesions, various disease states, and tortuous anatomy.

Despite the potential to improve restenosis rates associated with angioplasty and stenting in the coronary and peripheral vasculature, atherectomy is not commonly performed. The primary reason for this limited use is the cost, complexity and limited applicability of currently available devices. Many designs are unable to treat the wide range of disease states present in long complex lesions; luminal gain is often limited by the requirement of the physician to introduce multiple devices with increased crossing profiles; tissue collection is either unpredictable or considered unnecessary based on assumptions regarding small particle size and volumes; and optimal debulking is either not possible due to lack of intravascular visualization or requires very long procedure times. Based on these limitations current devices are likely to perform poorly in the coronary vasculature where safety and efficacy in de novo lesions, ostials, and bifurcations continue to pose great challenges.

Previously, atherectomy devices focused on macerating or emulsifying the atherosclerotic plaque such that it may be considered clinically insignificant and remain in the blood stream or aspirated proximally through small spaces in the catheter main body. The reliability of these devices to produce clinically insignificant embolization has been questioned when not aspirated through the catheter to an external reservoir. Aspiration requires a vacuum be applied to a lumen or annular space within the catheter to remove emulsified tissue. In early clinical evaluations of aspiration the presence of negative pressure at the distal working assembly cause the artery to collapse around the cutting element causing more aggressive treatment, dissections and/or perforations. In addition, the option for post procedural analysis of any removed disease is extremely limited or impossible. Atheromed, Pathway Medical and Cardio Vascular Systems, Inc. are examples of companies working on such product designs.

Other atherectomy devices include the directional atherectomy devices such as those developed by DVI and FoxHollow. These catheters use cupped cutters that cut and "turn" the tissue distal into a storage reservoir in the distal tip of the device. This approach preserves the "as cut" nature of the plaque but requires large distal collection elements. These large distal tip assemblies can limit the capabilities of the system to access small lesions and create additional trauma to the vessel.

Currently available atherectomy devices also do not include, and are poorly adapted for use with, real time image guidance. Physician practice is often to treat target lesion as if they contain concentric disease even though intravascular diagnostic devices have consistently shown significantly eccentric lesions. This circumferential treatment approach virtually ensures that native arterial wall and potentially healthy vessel will be cut from the vasculature.

Atherectomy catheter devices, systems and methods that may address some of these concerns are described and illustrated below.

SUMMARY OF INVENTION

Described herein are atherectomy catheters, systems including them and methods of using them. Some of the distinguishing features that may be included as part of these devices, systems and methods are summarized below.

In particular, described herein are atherectomy catheters devices described including one or more cutters configured to cut tissue that are actuated by longitudinal motion of a drive shaft, e.g., in the proximal/distal axis of the device. The same drive shaft may be used to rotate the cutter, which may be a ring-type cutter at a rotational speed appropriate for cutting the tissue. For example, the cutter may rotate at between about 200 and 5000 RPM (e.g., about 500 RPM, about 600 rpm, about 700 RPM, about 1000 RPM, etc.). Any of these variations may also include imaging such as optical coherence tomography (OCT) imaging configured to image the vessels tissue, including penetrating some depth into the vessel to image the tissue surrounding the blood vessel (such as the intima, media and externa layers). Imaging may help navigate as well as remove atheromatous plaques.

In general the imaging may include an optical sensor, such as an optical fiber end region when OCT is used, which may also rotate around the circumference of the device. This sensor region may be located proximally or distally to the cutter. The imaging sensor may include a lens and/or window through which light is transmitted. In general, the imaging sensor may be rotated around the periphery of the device. In some variations the imaging elements include OCT imaging elements that are off-axis within the catheter, which may be rotated manually or automatically for a number of turns in a first direction before rotating for a number of turns in a second direction. A separate drive shaft from the cutting drive shaft may be used to drive rotation of the imaging sensor, or the same drive shaft may be used. In general, the imaging sensor rotates at a much slower rate than the cutter. For example, the imaging sensor may rotates at about 30 RPM (e.g., between about 2 and about 50 RPM, between about 10 and 40 PM, between about 15 and 40 RPM, etc.). As mentioned, the imaging sensor may rotate approximately 10 time e.g., 5, 7, 8, 9, 10, 11, 12, 13, 14, 15, etc.) times around the circumference of the device clockwise before then switches direction to rotate counterclockwise for the same number of rotations, and switching direction again.

The cutter, which may be a rotating ring, may rotate in a single direction (e.g., clockwise, counterclockwise), or it may oscillate back and forth between clockwise and counterclockwise directions. The ring may have a sharp edge, a serrated edge, or the like.

In some variations, the catheter device also includes a handle having one or more controls for controlling the catheter. In addition, the devices or systems may also include one or more controls for controlling the rotation and/or oscillation of the annular cutting ring and/or the imaging system. The devices or systems may also include controls for an associate imaging (e.g., OCT) system. In some variations the device or system includes control logic for regulating the displacement and/or rotation and/or imaging. Proximal controls may include an automated advancement function to ensure proximal motion correlates to distal tracking in the vessel. In some variations, some or all of these controls may be on a handle, or may be on a separate controller.

Force limiting controls may also be used to ensure the input forces do not exceed what is required to effectively cut diseased tissue. This may reduce the chances of the device moving outside the perimeter of the lesion white activated thereby cutting into healthy arterial wall.

In some variations, the catheter systems described herein are compatible with 7F sheath access to the peripheral arteries, or 6F sheath sizes.

Any of these devices may also include one or more drive shafts (e.g., a cutter drive shaft and/or an imaging drive shaft) extending along the length of the catheter body. For example, the cutter drive shaft may comprise a cable drive shaft having a distal gear configured to drive rotation of the cutting ring. In some variations, the annular cutting ring comprises internal gear teeth configured to mate with a drive shaft to rotate the cutting ring.

The drive shaft may be directly connected to the annular cutting ring. For example, the drive shaft comprises a hollow tubular drive shaft. Similarly, the imaging drive shaft (in variations having a separate imaging drive shaft) may be directly connected to the optical head that rotates, or the rotation may be geared. The optical and cutting drive shafts may be coaxially arranged. For example, the cutting drive shaft may be surrounded by the imaging drive shaft; a lubricious fluid and/or intermediary layer may be positioned between the drive shafts. In some variations the drive shafts may be coaxially positioned relative to each other. Alternatively, in some variations, the drive shafts are parallel to each other within the lumen of the catheter.

In some variations the imaging element is driven off of the same drive shaft that moves the cutting element, but at a different rate; thus the imaging element may be geared down (or the cutting element may be geared up) to drive the imaging sensor and cutting element at different rates.

Any of the catheters described herein may include a guidewire lumen extending the length of the catheter. The lumen may be centered or off-centered, and one or more additional lumens may also be included.

In some variations, the annular cutting ring may form an outer surface of the catheter in both the closed and open configurations.

In some variations the distal tip region of the catheter is deflected off-axis from the proximal region of the catheter and cutter, to expose the rotating cutting edge of the cutter and allow it to cut tissue. For example, the catheter may be configured so that lateral movement of the cutter drive shaft causes the distal end of the catheter to displace (e.g., bend) away from the cutting ring, exposing it so that it may cut tissue. The distal end of the device may bend at an angle for the immediately adjacent proximal region of the catheter, and/or it may displace off-axis, as described in the U.S. Ser. No. 12/829,277, titled "ATHERECTOMY CATHETER WITH LATERALLY-DISPLACEABLE TIP," which was previously incorporated by reference. The distal tip region may also be moved back into line with the proximal region of the catheter, preventing further cutting. Other variations are also described herein, including variations in which lateral movement of the cutting element extends the cutting element radially from the side of the catheter, where it may engage with the wall of the vessel. Other variations include oscillating cutters.

Some variations of the atherectomy catheter devices may also include an internal tissue collection region configured to receive tissue cut by the annular cutting ring. For example, the tissue collection region may be located within the distal tip assembly. The tissue collection region may be located within the catheter body.

As mentioned, in any of these variations, the catheter may include an OCT imaging subassembly. For example, the OCT imaging subassembly may include a fiber optic extending the length of the catheter body. The OCT imaging assembly may comprise a side-facing OCT emitting element fixed proximal to the annular cutting ring. Alternatively, the OCT imaging assembly may include a side-facing OCT emitting element fixed distally to the annular cutting ring.

For example, described herein are atherectomy catheter devices configured to visualize and to cut tissue. Such devices may include: a distal tip; a cutter proximal to the distal tip, the cutter having a cutting edge that is configured to rotate; an imaging sensor proximal to the cutter and configured to rotate independently of the cutter; and a cutter drive shaft coupled to the cutter and configured to rotate the cutter wherein the cutter drive shaft is further configured to be longitudinally displaced proximally or distally to deflect the distal tip to expose the cutting edge of the cutter.

The device may also include a ramped slide surface between the distal tip and a region of the catheter proximal to the cutter, wherein the ramped slide surface is configured to guide deflection of the distal tip as the cutter drive shaft is moved longitudinally. The device may also include an imaging drive shaft coupled to the imaging sensor and configured to rotate the imaging sensor. The imaging drive shaft may be located coaxially to the cutting drive shaft. For example, in some variations the imaging drive shaft is positioned within the cutting drive shaft. In some variations the catheter does not include a separate drive shaft for the imaging and cutting elements, but a single drive shaft is used with gears to step up or step down the rate of rotation so that the cutter may be rotated more rapidly than the imaging drive shaft. Also, in general, the imaging drive shaft may be configured to alternately rotate the imaging sensor clockwise and counterclockwise, particularly in variations in which the imaging sensor element is an OCT imaging element having an off-axis optical fiber within the catheter.

Thus, as just indicated, in some variations the imaging sensor comprises an OCT imaging sensor, and in some variations the imaging sensor comprises a fiber optic extending off-axis along the longitudinal length of the catheter.

The cutter may be a ring cutter; for example, the cutter may be a complete or partial ring of metal having a cutting edge that is exposed only when the distal tip region is displaced. In general, the distal tip region may be displaced by sliding it at least slightly off-axis, and in some variations, also bending it away from the longitudinal axis of the catheter (relative to the region of the catheter just proximal to the distal tip region). Thus, in some variations, the slider region may be used to guide the deflection of the distal tip region.

The distal tip may be hollow, and in some variations may be clear. The distal tip region may be configured to collect tissue cut by the cuter. In some variations the distal tip region is configured to be removable (and/or replaceable). For example, the distal tip may be threaded or otherwise removably secured to the distal end of the catheter. The distal tip region may include a flush port to allow removal of the cut material collected therein.

In any of the variations described herein, the catheters may include a proximal handle having a first driver for driving rotation of the cutter and a second driver for driving rotation of the imaging sensor.

For example, described herein are proximal handles having a first driver for driving rotation of the cutter between 100 and 10,000 rpm, and a second driver for driving rotation of the imaging sensor at less than 100 rpm. As mentioned, the proximal handle may include a first driver for driving rotation of the cutter in a first direction and a second driver for alternately driving rotation of the imaging sensor in a first rotational direction and a second rotational direction.

Also described herein are atherectomy catheter devices configured to visualize and to cut tissue that include: a distal tip; a cutter proximal to the distal tip, the cutter having a cutting edge that is configured to rotate; an imaging sensor proximal to the cutter and configured to rotate independently of the cutter; a cutter drive shaft coupled to the cutter and configured to rotate the cutter wherein the cutter drive shaft is further configured to be longitudinally displaced proximally or distally to deflect the distal tip to expose the cutting edge of the cutter; and an imaging drive shaft coupled to the imaging sensor and configured to alternately rotate the imaging sensor clockwise and counterclockwise.

Some variations of the catheters described herein do not necessarily include imaging (e.g., OCT imaging or other imaging modalities), although OCT imaging may be incorporated into any of them. For example, described herein are atherectomy catheter devices having: a distal tip; a cutter proximal to the distal tip, the cutter having a cutting edge that is configured to rotate; and a cutter drive shaft coupled to the cutter and configured to rotate the cutter wherein the cutter drive shaft is further configured to be longitudinally displaced proximally or distally to deflect the distal tip to expose the cutting edge of the cutter. The device may also include a proximal handle having a control for controlling the longitudinal displacement of the cutter drive shaft.

Also described herein are atherectomy catheter devices including: a distal tip; a cutter proximal to the distal tip, the cutter having a cutting edge that is configured to rotate; a cutter drive shaft coupled to the cutter and configured to rotate the cutter; and a ramped slide surface between the distal tip and a region of the catheter proximal to the cutter, wherein the ramped slide surface guides deflection of the distal tip to expose the cutting edge of the cutter.

Another variation of an atherectomy catheter device as described herein for visualizing and cutting tissue may include: a distal tip; a cutter proximal to the distal tip, the cutter having a cutting edge that is configured to rotate; an imaging sensor proximal to the cutter and configured to rotate independently of the cutter; a cutter drive shaft coupled to the cutter and configured to rotate the cutter; and a ramped slide surface between the distal tip and a region of the catheter proximal to the cutter, wherein the ramped slide surface guides deflection of the distal tip to expose the cutting edge of the cutter.

Methods of operating an atherectomy device, and/or for performing an atherectomy are also described. For example, described herein is a method for operating an atherectomy device comprising deflecting the distal tip region of an atherectomy catheter by driving the distal tip region against a ramped slide surface to displace the distal tip region and expose a rotatable cutter; rotating the cutter at a first rate between 100 and 10,000 rpm; and rotating an imaging element located proximal to the cutter on the catheter at a rate that is less than 100 rpm while imaging. As mentioned, the imaging element (e.g., the end of the fiber optic in an OCT imaging modality) may be alternately rotated clockwise and then counterclockwise; in some variations the imaging element is rotated first clockwise a predetermined number of rotations (e.g., between 1 and 20, such as 9, 10, 11, 12, etc. rotations) then counterclockwise the same number of rotations.

Deflecting the distal tip may include moving a rotatable drive shaft within the catheter longitudinally to displace the distal tip.

Also described herein is a method of operating an atherectomy device, the method comprising: deflecting the distal tip of an atherectomy catheter by moving a drive shaft of the catheter longitudinally to drive a distal tip region of the catheter against a ramped slide surface and thereby to displace the distal tip region and expose a rotatable cutter; rotating the cutter at a first rate between 100 and 10,000 rpm; and rotating an imaging element located proximal to the cutter on the catheter alternately clockwise and counterclockwise at a rate that is less than 100 rpm.

Any of the atherectomy devices described herein may be used without imaging, and may therefore be adapted for use without an imaging sensor (e.g., mirror, fiber, etc.). Thus, in one variation an atherectomy device may be configured to allow axial pushing or pulling of a member (e.g., a torque shaft) to displace the distal tip region and expose the cutting member.

Also described herein are imaging catheters or imaging wires having an optical fiber (e.g., for use with an OCT imaging sensor) that is configured to wrap around a central wire or fiber which may be configured as a drive shaft. These imaging catheters may be used without (or as part of) an atherectomy device or system. The distal end of the fiber is coupled (e.g., glued, epoxied, etc.) to the rotatable distal end of the imaging wire, and the distal end and end of the imaging fiber may be rotated by rotating the central drive shaft. The portion of the imaging catheter proximal to the rotating distal tip region (which may be referred to as a torque shaft) does not rotate with the tip region, and may remain stationary relative to the distal tip. In operation, the optical fiber connected to the distal may wrap around the central wire/fiber, and may be configured to allow numerous (up to a few hundred) rotations in a first direction (e.g., clockwise) before having to rotate counterclockwise, and then cycling back through clockwise rotations again. In some variations the catheter may include a central lumen through which fluid (e.g., saline) may be flushed, with one or more flushing ports located distally to allow flushing to clear the imaging pathway.

Also described herein are variations of imaging catheters in which both the distal end of the catheter and the torque shaft region of the catheter rotates while the centrally located optical fiber twists. In this variation the distal end of the optical fiber is configured as the imaging sensor, and is fixed to the rotating imaging head. The more proximal end of the fiber is fixed relative to the rotating distal tip. As the distal tip rotates, the fiber is allowed to twist and rotate; although this would seem to damage the optical fiber, in practice the fiber may be rotated in this manner though hundreds of complete rotations without substantially degrading in signal transmission or structure.

BRIEF DESCRIPTION OF THE DRAWINGS

FIGS. 2A-2B show the exemplary device of FIG. 1 in an inactive or closed configuration (with the distal tip covering or protecting the cutting edge of the cutter) and in an open configuration (with the distal tip deflected to expose the cutting edge of the cutter), respectively, FIG. 3A shows another view of the distal portion of a catheter such as the one shown in FIGS. 1-2B. This example shows the distal tip region which is absent in FIGS. 1 and 2A-2B.

FIG. 3B shows an enlarged view of the distal end region of FIG. 3A.

FIGS. 5A and 5B show another view of the hinged region of the catheter shown in FIGS. 4A-4C; in FIG. 5B some elements have been removed to more clearly show the ramped slide surface between the distal tip and a region of the catheter proximal to the cutter. Pushing or pulling on the actuator (e.g., a drive shaft) proximally/distally may deflect the distal tip region out of the longitudinal axis relative to the rest of the catheter immediately proximal to the distal tip region.

in FIG. 7B some elements have been removed to ore clearly show the ramped slide surface.

FIGS. 8A and 8B show side and end views, respectively, of a more distal region of the catheter, partially cut away to illustrate two drive shafts, one for controlling rotation of the cutter, surrounding one for controlling rotation of the imaging sensor (e.g., OCT fiber).

FIG. 9A shows one variation of a handle for an atherectomy catheter as described herein; FIG. 9B shows a perspective view of an accessory device for holding the catheter and/or a guidewire.

FIGS. 11-14B illustrate one variation of an atherectomy catheter having a cutting element.

FIGS. 19A and 19B show two variations of imaging guidewires and illustrate an alternative optical fiber management technique that may be used.

FIG. 20 illustrates another variation of an imaging guidewire.

FIG. 21A shows another variation of a distal end portion of an atherectomy catheter including an imaging sensor.

FIG. 21B shows another configuration of an imaging sensor and cutter in which the cutter and imaging sensor rotate together and fiber optic of the imaging sensor is centrally located; the fiber optic management is similar to the variation shown in FIG. 20.

DETAILED DESCRIPTION OF THE INVENTION

Figure 1:
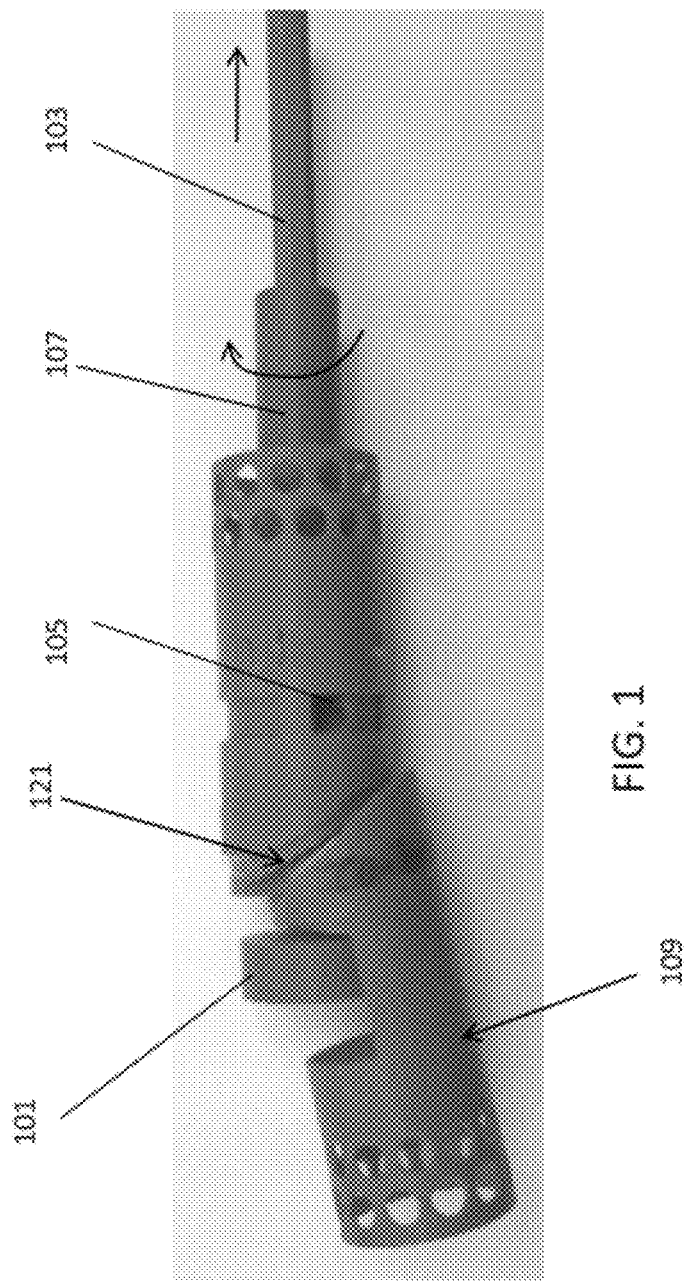
FIG. 1 shows one variation of a portion of an atherectomy catheter for both cutting and/or imaging within a vessel. This variation has a longitudinally displaceable distal tip region; the distal tip may be displaced by pushing or pulling (e.g. proximally/distally) an actuator within the catheter and thereby expose a cutting edge of the rotational cutter.

In general the atherectomy devices described herein include one or more cutters configured to cut tissue that are actuated by longitudinal motion of a drive shaft. By "actuation" the cutter may be exposed to the tissue so that it may cut. The cutting drive shaft may be rotatable as well and may also move longitudinally (e.g., forward and backwards along the long axis of the catheter). The longitudinal motion to expose the cutter may be controlled manually or automatically, and may cause deflection of the distal tip region out of the axis of the more proximal region of the catheter; in some variations it may move the catheter laterally out of the long axis of the catheter. Typically any of these catheters may also include an imaging system for imaging the walls (and into the walls) of the vessel, e.g., using an off-axis OCT imaging system that rotates at a much slower rate around the perimeter of the catheter than the cutting edge rotates for cutting. Thus, in some variations, the device an elongate catheter body, and a rotatable OCT imaging element having a fiber optic extending off-axis within the elongate catheter body. In some variations the catheter body also contains two drive shafts: an imaging drive shaft and a cutting drive shaft. The two drive shafts may be concentrically arranged, while the imaging drive shaft rotates at a much lower speed (and in alternating directions) compared to the cutting drive shaft.

In variations having two drive shafts, both drive shafts may be a flexible; the cutting drive shaft in particular may have sufficient column strength to push or pull to activate the rotating cutter by longitudinally moving (e.g., a slight longitudinal movement) proximally-to-distally along the longitudinal length of the catheter. In some variations the longitudinal movement of the cutting drive shaft deflects the distal tip away from (or back to) the long axis of the more proximal region of the catheter, exposing the rotating cutter and allowing it to cut. In other variations the longitudinal movement of the drive shaft pushes or drives the cutting element away from the long axis of the catheter, exposing the cutting edge to allow cutting. The driving movement does not need to be substantial (e.g., a few millimeters of movement may be sufficient). The catheter may also include a longitudinal lock to hold the catheter with the cutting element exposed.

Described herein are variations of atherectomy devices having longitudinal actuators.

For example, FIGS. 1-10 illustrate variations of atherectomy catheters including both a rotational cutter and imaging sensor. The devices shown in FIGS. 1-10 typically include one or all of the following features: rotating cutter located proximal to a deflectable distal tip, an imaging sensor, and at least one drive shaft configured to rotate the cutter; a separate drive shaft my also be used to rotate the imaging element. In some variation one or both drive shafts may also be used to actuate displacement of the distal tip and therefore expose the cutter. Other features are described below in the specific examples; it should be understood that these features may be generally used in combination with any of the other features described.

Cutter

Any appropriate cutter may be used. Typically the cutter is a ring or partial ring cutter that is rotated by connection with a cutting drive shaft. The cutting drive shaft rotates to drive rotation of the cutter. One or more edges of the ring may be configured to cut. For example, the cutter may include at least one cutting edge that is typically not exposed until the distal tip region is deflected out of the way. The cutting edge may be sharp, smooth, serrated, etc. In some variations the cutting edge is configured to face distally. The cutter may be made of any appropriate material, including a metal, ceramic, polymeric, or composite material, or the like.

When not exposed, a portion of the cuter may form a portion of the outer surface of the catheter; for example, a side wall of the cutter may form a portion of the outer surface of the catheter.

Distal Tip Region

The distal tip region is configured to deflect to expose the cutting surface of the cutter. The distal tip region may be hollow or otherwise configured to hold material cut by the atherectomy device. In some variations the distal tip region is clear or at least partially transparent, allowing one to see if material has been collected or remains in the tip region. The distal tip region may include a flush port or may otherwise be adapted to allow removal of cut material stored therein. For example, the distal end may be tapered but may be open. The distal tip region may be removable and/or replaceable. A reusable locking mechanism, such as threads, or the like, may be used to secure a distal tip region on the catheter.

In some variations the distal tip region is relatively stiff; in other variations the distal tip region is flexible, and may be formed of a soft or resilient material. For example, the distal tip region may be a mesh or woven material.

In general, the distal tip region is deflectable. Typically, the distal tip region is deflectable so that it is displaced away from the axis of the catheter, thereby exposing the cutter. The cutter therefore remains in the same radial position both in active and inactive configurations, while the distal tip region is deflected. For example, the distal tip region may be deflected off-axis of the long axis of the catheter; thus, the distal tip region may be dropped radially away from the longitudinal axis of the catheter. The distal tip may also or alternatively be angled away from the rest of the catheter (e.g., the region of the catheter proximal to the distal tip region).

Typically, the interface between the distal tip region and the rest of the catheter may be configured as a ramped slide surface. This slide surface is angled relative to a plane perpendicular through the long axis of the catheter, though the direction of the angle determine if the distal tip region is deflected by pushing or by pulling the actuator (e.g., the cutting drive shaft). The ramp ramped slide surface is configured to guide deflection of the distal tip as the cutter drive shaft is moved longitudinally.

Imaging Sensor

Any of the catheters described herein may include an imaging sensor. The imaging sensor may be, in some variations, configured to rotate independently of the rotating cutter to allow visualization of the vessel. An imaging sensor may rotate independently of the rest of the catheter, including the cutter. In some variations, the cutter may rotate at a much faster rate (10×-100× faster) than the imaging sensor. The imaging sensor may also rotate in more than one direction (e.g., first clockwise for some number of rotations, then counterclockwise for some number of rotations). In contrast, the cutter may be configured to rotate in a single direction.

In general, an imaging sensor captures images of the lumen, or into the wall of the lumen. The imaging sensor may provide real-time images from before, during and/or after cutting when used as part of an atherectomy device. In any of the variations described herein the imaging sensors may be OCT imaging sensors. An OCT imaging sensor may include an optical fiber, a mirror to direct the light into the tissue and back into the fiber for processing. The sensor may therefore include an optical fiber. This fiber may be held off-axis within the catheter. The distal end (e.g., imaging sensor end) of the optical fiber may be secured to allow rotation of the distal end of the fiber, while the region between the proximal end (which may be fixed) and the distal end (which may be fixed to a rotating head) is allowed to rotate somewhat freely within the catheter body, and therefore to wind and unwind around within the catheter body as the imaging sensor end is rotated. As mentioned, the distal end of the optical fiber may form an imaging sensor that may include a mirror to allow imaging of the inside of a vessel as the imaging sensor is rotated. The unrestrained optical fiber may be held in a channel, passage, tube, or other structure that constrains its ability to kink or knot up on itself as it is rotated. In some variations the optical fiber may be configured to wrap around a wire, shaft, tube, or the like. In some variations, the optical fiber does not wrap around anything, but twists on itself. In general, systems including optical fibers may limit the number of rotations clockwise and counterclockwise, and may alternate between clockwise and counterclockwise rotation to allow continuous imaging when desired.

Drive Shafts

As mentioned, the devices may include a drive shaft for rolling rotation of the cutter, and (in some variations) a separate drive shaft for controlling rotation of the imaging sensor. For example, a cutting drive shaft may be connected to the rotatable cutter and may also be coupled to a drive (e.g., motor) in proximal end of the catheter such as the handle to drive rotation of the cutter. A separate imaging drive shaft may be coupled to the imaging sensor for driving rotation of the imaging sensor. In some variations a drive shaft, such as the cutting drive shaft, may also be used to actuate deflection of the distal tip region.

An alternate variation of the devices described herein may include a single drive shaft that rotates from which rotation of both the cutter and the imaging sensor may be achieved. For example, the distal end may include gears for stepping down (or up) the rotation rate of the drive shaft to drive rotation of either the cutter or imaging element. In addition, in some variations a separate actuator may be used to control deflection of the distal tip region. For example, the distal tip region may be deflected by a tendon or other member (e.g., a member having a high column strength) extending the length of the catheter.

EXAMPLES

FIGS. 3A and 3B show one variation of an atherectomy catheter that includes both rotating cutter and a rotating imaging sensor. In this variation the cutter and imaging sensor may be rotated separately, and the distal tip region may be displaced to expose the cutting edge of the cutter, allowing material to be removed. OCT images may be collected continuously (in a 360 degree view before, during, or after cutting. In this variation the cutter is positioned distally to the imaging sensor. The distal tip region may be displaced by applying pulling (or in some variations pushing) force to the drive shaft of the cutter, which displaces the distal tip region. Moving the drive shaft laterally (e.g., proximally or distally) to displace the distal tip does not otherwise effect the operation of the cutter, which may continue to rotate. This may allow the distal tip region to help control the thickness of slices cut from the tissue by controlling the amount that the cutting edge is exposed.

Referring now to FIG. 1, FIG. 1 shows a portion of one variation of an atherectomy catheter configured for both cutting and/or imaging. The portion illustrated in FIG. 1 is the hinge region between the distal tip region (not shown and the more proximal elongate region of the atherectomy catheter. FIG. 1 shows a rotatable cutter 101 coupled to a cutting drive shaft 103. The drive shaft may be rotated to move the cutter. The device also includes an imaging sensor 105 that is coupled to an imaging drive shaft 107. The imaging drive shaft may be rotated to rotate the imaging sensor, and may be rotated independently of the cutter and cutter drive shaft. In this example, the imaging drive shaft coaxially surrounds the cutter drive shaft.

The distal tip region 109 (which may include a distal tip region chamber for holding material removed by the device as shown in FIGS. 3A and 3B), is shown deflected downwards and slightly off-axis, exposing the rotating cutter 101. In this example, the distal tip region may be deflected by pulling proximally on the cutter drive shaft 103, as indicated by the right pointing arrow above the cutter drive shaft. Pulling the cutter drive shaft forces the distal tip region against the angled face of the ramped slide surface 121 formed between the proximal end of the catheter and the distal end region. This ramped slide surface may be configured so that the distal tip region first drops "down," e.g., displaces longitudinally but remains substantially parallel to the elongate body of the catheter. In some variations, with the application of continued pulling (or in some variations pushing) the distal tip region bends at an angle away from parallel with the rest of the catheter, as shown.

FIGS. 2A and 2B illustrate the same region of the device of FIG. 1 in both a non-cutting configuration and a cutting configuration, respectively. In the non-cutting configuration, the catheter extends along a single longitudinal axis (which may be curved, as the catheter is flexible), and the cutting edge of the cutter is not exposed to the tissue. The cutter may be rotated, but rotation will not typically cut tissue until the distal tip region is moved out of the way, as shown in FIG. 2B. In FIG. 2B, the distal tip region 109 is shown deflected away from the cutting edge 203. Typically, once the distal tip region 109 is deflected to expose the cutting edge, no additional force is necessary on the cutting drive shaft (or other actuator) to keep the cutting edge exposed.

Returning now to FIG. 3A, the distal end region (including a chamber for holding cut tissue 303) of an atherectomy catheter including the cutter, hinge region and imaging sensor shown in FIGS. 1-2B are shown. FIG. 3B shows an enlarged view of the distal end of the device of FIG. 3A. In this example, the distal end region 303 may be configured as hollow and may be used to store material cut by the atherectomy device. As the device is advanced with the cutter exposed, material cut may be pushed against the inside surface of the rotating cutter and may then be deflected back into the hollow distal tip region. The distal tip region may also include an opening 314. A proximal handle or handles to control the catheter (including the imaging sensor and/or cutter) is not shown in FIG. 3A or 3B, but is described below.

Figure 4A:
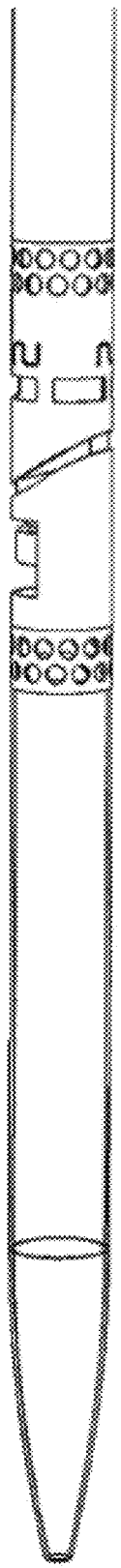
FIGS. 4A-4C show different rotational views of the distal region of an atherectomy catheter configured for both visualization and/or cutting.
Figure 4B:
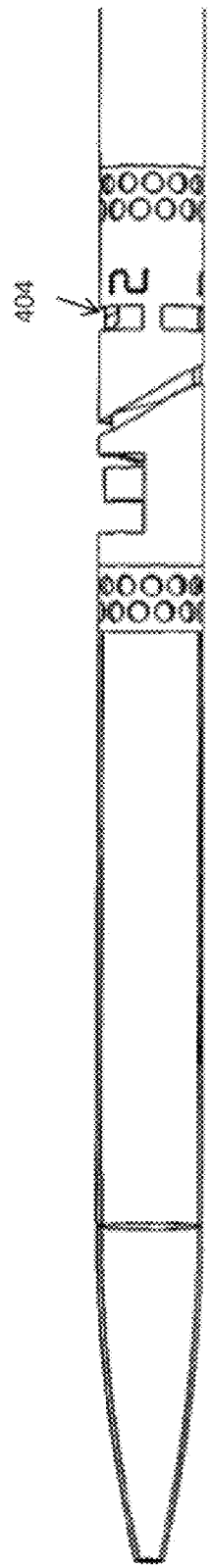
Figure 4C:
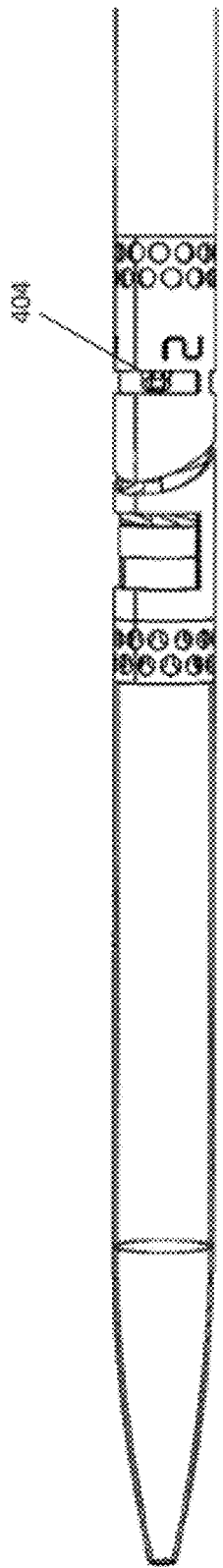

FIGS. 4A-4C illustrate a distal end region of this variation of the device, from different views than those shown in FIGS. 3A and 3B. For example, In FIG. 4C, the imaging element 404 is configured as an OCT imaging sensor element as previously described. In this embodiment, the imaging sensor include the distal end of the optical fiber that is fixed to a rotatable chassis including a mirror for directing the optical signal out from the catheter and into the walls of the vessel. In some variations the imaging element is directed out at 90 degrees from the catheter (looking laterally); in other variations the imaging element is configured to look forward or slightly forward, or backwards. The imaging sensor may also be configured to rotate completely around the perimeter of the catheter, as illustrated in FIGS. 1-4C. The imaging sensor may be configured so that the end of the optical fiber is secured fixed (e.g., epoxied) into position on a rotatable chassis (not visible in FIGS. 3A-4C. A surrounding housing, which may form part of the outer catheter wall, may include one or more windows or viewports through which imaging may occur. These viewports may be separated into discrete regions, and the separators may also act as fiduciary markers, particularly when arranged in a non-rotationally symmetric configuration. For example, the viewports may be formed by holes in the outer catheter shaft separated by 90°, 90° and 180°. Thus, as the imaging sensor is rotated, the view may be periodically interrupted by separators at 0°, 90°, 270° and again back at 0°/360°. Such separations may therefore be used to indicate the orientation of the catheter within the body.

As mentioned, the catheter may be configured so that the imaging sensor is sequentially rotated both clockwise and counterclockwise. For example, the imaging sensor may be configured so that after a number of rotations clockwise, the imaging sensor is then rotated counterclockwise for the same number of rotations, and this cycle may be repeated. In variations in which the imaging element is an off-axis optical fiber, the fiber may therefore wind and unwind around the inside of the catheter (e.g., around the drive shaft or shafts, in some variations).

Figure 4D:
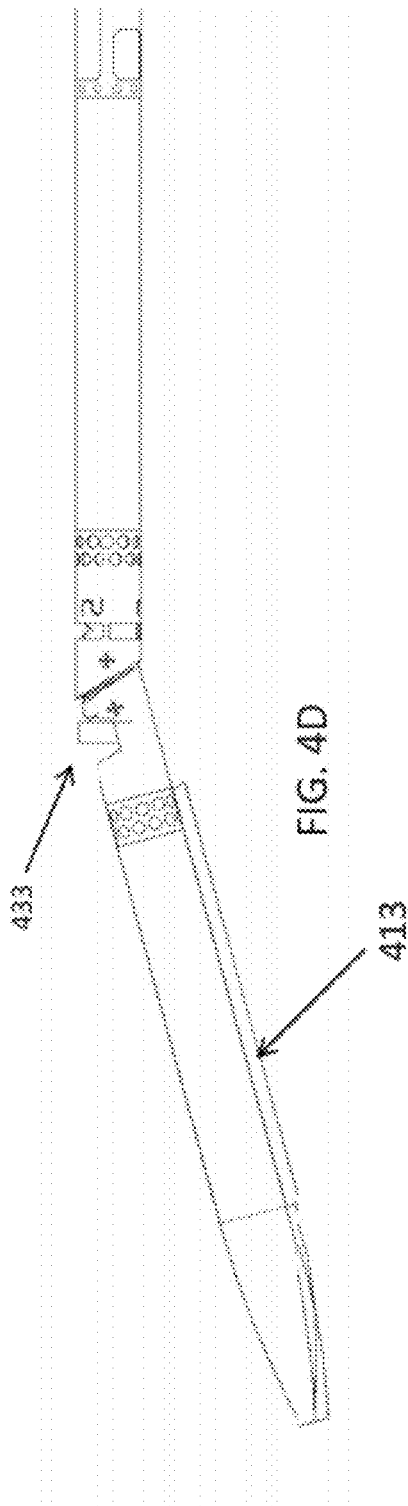
FIGS. 4D and 4E show the catheter of FIGS. 4A-4C with the cutter exposed by deflecting the distal tip region; this variation also include a guidewire channel (e.g., guidewire exchange channel) that may be included in any of these catheter variations.
Figure 4E:
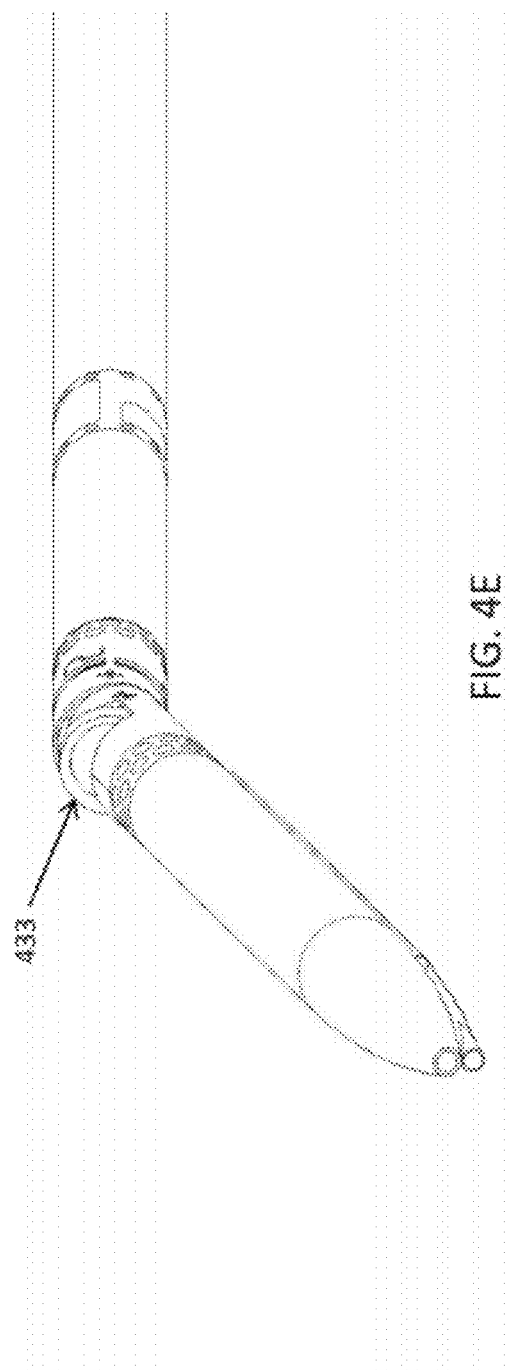
Figure 4F:
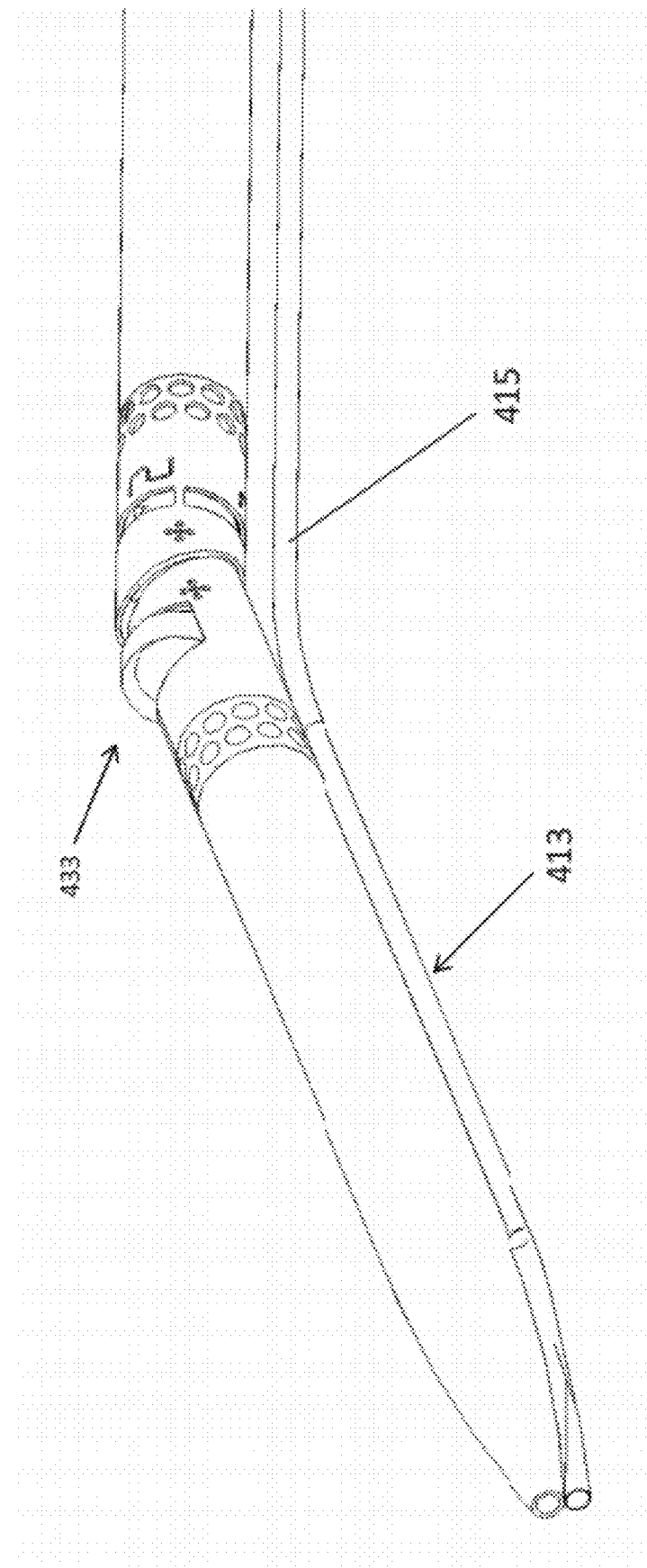
FIG. 4F shows a variation in which a guidewire is present within the guidewire channel.
Figure 6A:
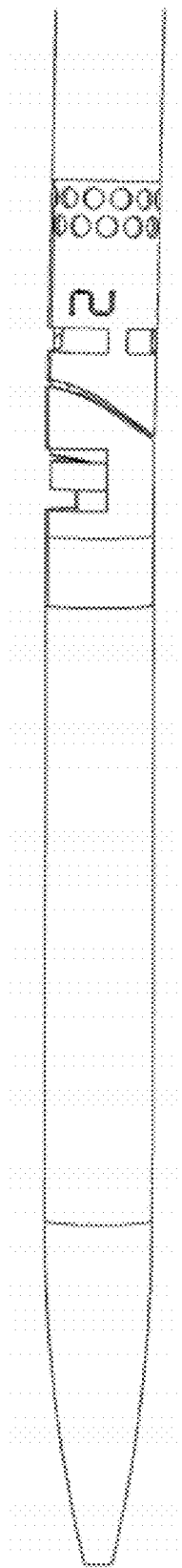
FIGS. 6A and 6B illustrate another variation of a catheter device in which the ramped slide surface extends in the opposite direction from the device shown in FIGS. 5A and 5B.
Figure 6B:
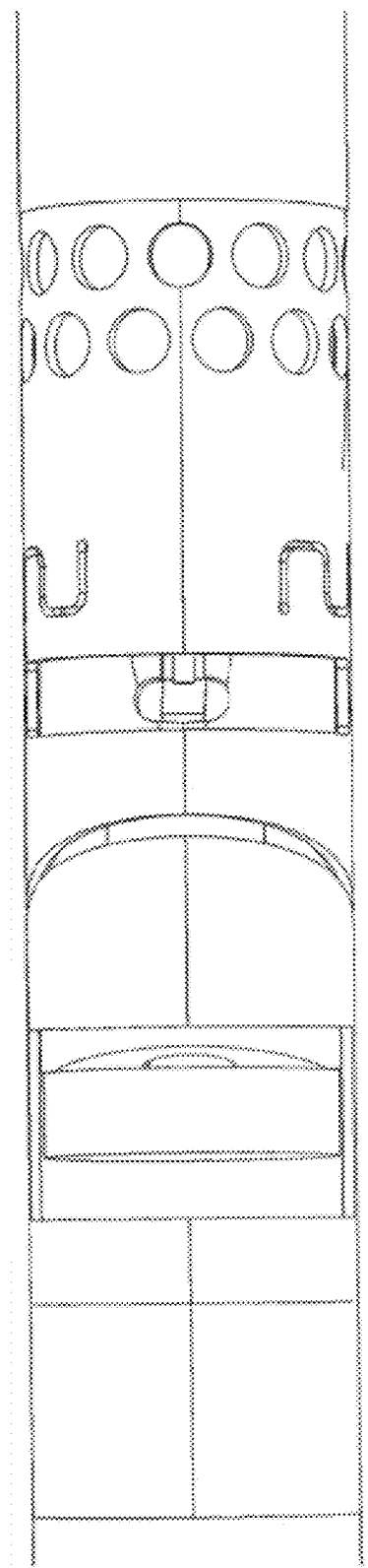
Figure 7A:
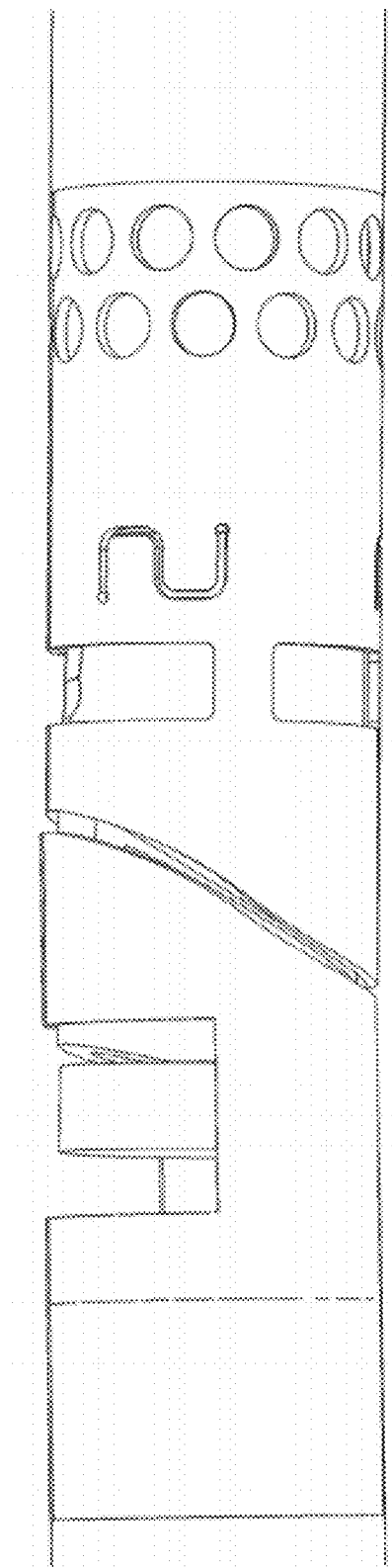
FIGS. 7A and 7B show another view of the hinged region of the catheter shown in FIGS. 6A and 6B.
Figure 7B:
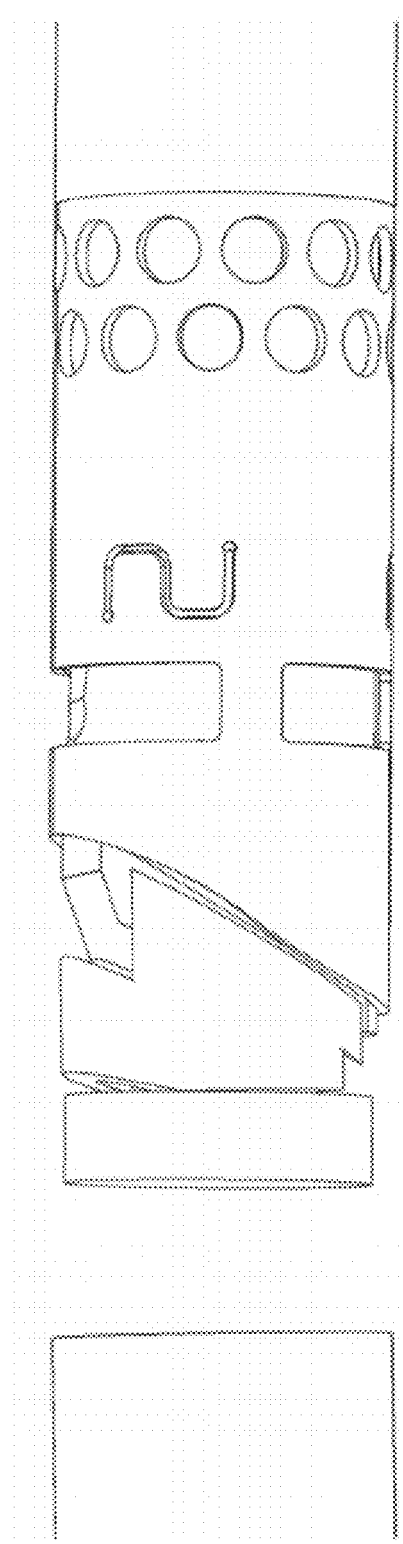

FIGS. 4D-4F show side perspective views of the atherectomy device variation shown in FIGS. 4A-4C in which the distal tip region has been displaced as discussed above. In these variations the catheter is also shown with a guidewire attachment region 413 into which a guidewire 415 may be threaded, as illustrated in FIG. 4F. Thus, the catheters described herein may be used with a guidewire 415 that has been placed within the body, including across an occluded region. The guidewire attachment region may be a rapid exchange type connection.

FIG. 4E shows a proximally-looking view of the catheter, showing the cutting region exposed by displacing the distal tip down and bending away from the long axis of the catheter. The side of the cutting opening formed 433 may be regulated by how much the drive shaft (e.g., the cutter drive shaft) is pushed or pulled distally/proximally, and therefore how much the distal tip is displaced. The catheter may be configured to lock the proximal/distal position of the drive shaft and therefore maintain a selected cut opening size.

FIGS. 5A and 5B show a slightly enlarged view of a hinge or pivoting region of an implant such as those illustrated above, showing the cutter, imaging, sensor and the ramped slide surface. As used herein, a ramped slide surface may be a cam surface, and may include any surface or interface between the two regions of the catheter in which longitudinal force (e.g. pushing or pulling) from one end of the implant results in radial displacement of the distal tip region, exposing the cutting edge of the cutter.

As mentioned, an atherectomy catheter such as the one shown in FIGS. 1-4F above may be configured so that the distal tip region is displaced either by pushing or by pulling an actuator. In many of these examples the actuator is a drive shaft, though other actuators may be used, including the imaging drive shaft, and/or a dedicated actuator, which may be a cable, shaft, or the like. FIGS. 1-4F illustrate a variation in which the distal tip region is displaced (revealing the cutting edge) by pushing the cutting drive shaft distally, and replacing the distal tip region (protecting the cutting edge) by pulling proximally on the cutting drive shaft. Other variations, such as those described in FIGS. 6A-7B are configured to displace the distal end and form a cutting opening by pulling an actuator (e.g., the drive shaft) proximally and restoring it to an original position by pushing the actuator distally.

As may be seen by comparison, for example, of FIGS. 7A and 7B to FIGS. 5A and 5B, altering the actuator direction in this manner may be achieved by changing the direction of the ramped slide surface, and in some variations, the addition of structures to translate the actuator force into displacement. For example, in FIGS. 6A-7B, the ramped slide surface is angled in an opposite orientation from that shown in FIGS. 4A-5B.

In general, in the atherectomy device variations illustrated in FIGS. 1-7B, the imaging sensor and the rotating cutter are driven separately, using separate drive shafts. Other variations, in which the imaging sensor and cutter are rotated together are also contemplated and described below. In some variations, the rotation of the imaging sensor is dependent upon (e.g., based on) the rotation of the cutter.

FIGS. 8A and 8B show partial views of the more proximal region of an atherectomy catheter, showing the arrangement of the outer imaging drive shaft 801 surrounding an inner cutter drive shaft 803; the two drive shafts may be rotated independently. In some variations the inner drive shaft may be separated from the outer drive shaft at least along a portion of its length by a lubricant or lubricious material. A lubricant may be or may include water. FIG. 8B shows an end view of the proximal end, looking down the shaft; the fiber optic 804 may wrap in the space 811 between the inner drive shaft 803 for the cutter and the outer drive shaft 801 for the imaging sensor. The distal end of the optical fiber 804 is glued to a rotating chassis (not visible) along with the mirror 809 (the outer drive shaft 801 has been made partially transparent in this view. Thus, in this variation the distal end of the optical fiber is secured to the rotatable chassis and the proximal end of the optical fiber (not shown) is secured to the handle, while the intermediate region between the two ends is allowed to wrap within the catheter.

Any of the variations described herein may also include a rinse or flush port that is located near the imaging sensor to allow fluid (e.g., saline) to be flushed from the catheter to clear debris or red blood cells (which may otherwise occlude or degrade the field of view). For example, fluid may be pressurized and released from the region of the catheter near the imaging sensor to rinse the imaging sensor. This rinse may occur continuously or when controlled by the user. For example, fluid from between the two drive shafts may be pressurized to flush the imaging sensor. The rotatable imaging chassis may be configured with one or more flush ports for this purpose; the proximal end region of the catheter may include a port for applying and/or pressurizing fluid.

Figure 10:
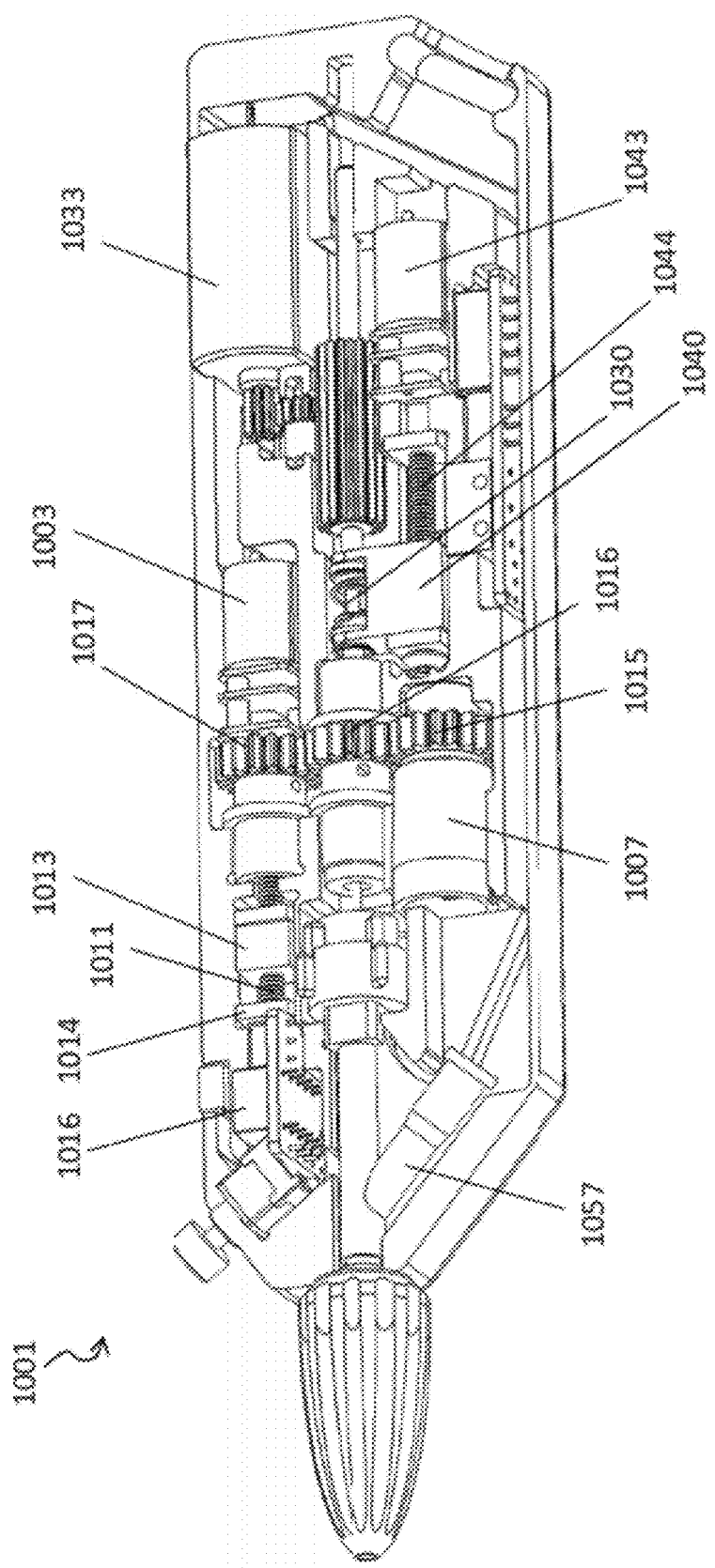
FIG. 10 shows a side perspective view of the handle shown in FIG. 9A, in which the outer covering has been removed to illustrate some of the internal features, including two separate driver (e.g., motors) for rotating the cutter and imaging sensor, respectively.
Figure 11:
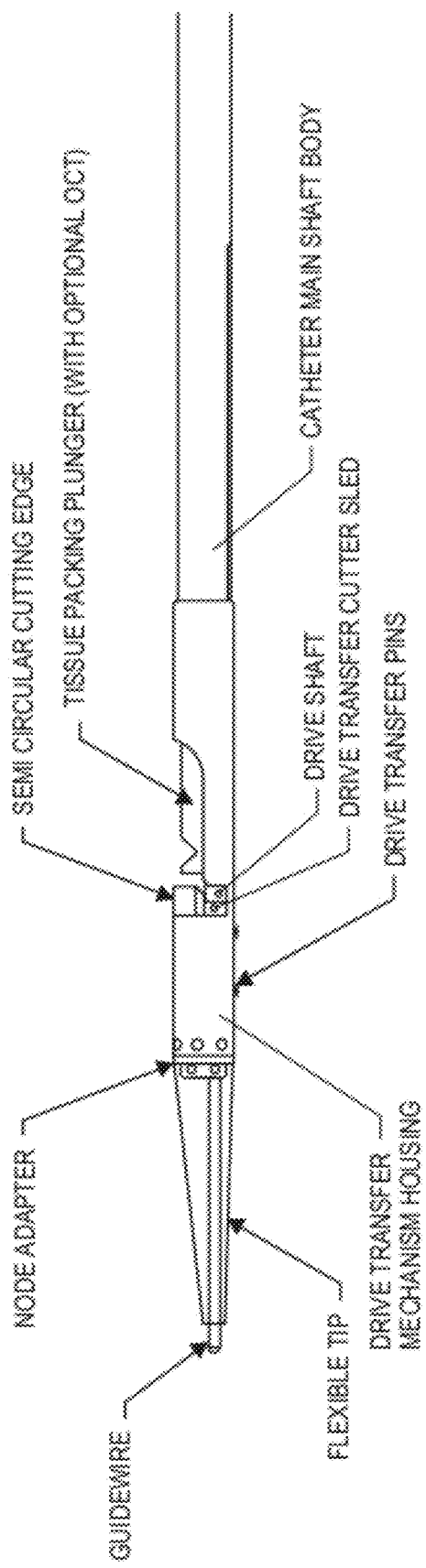
Figure 12A:
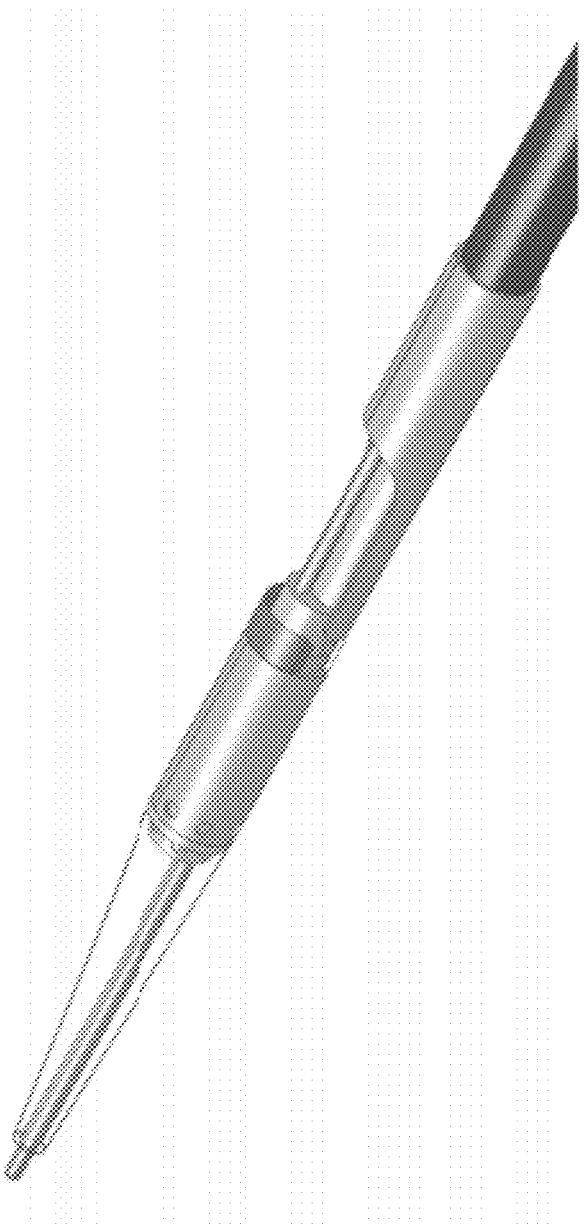
Figure 12B:
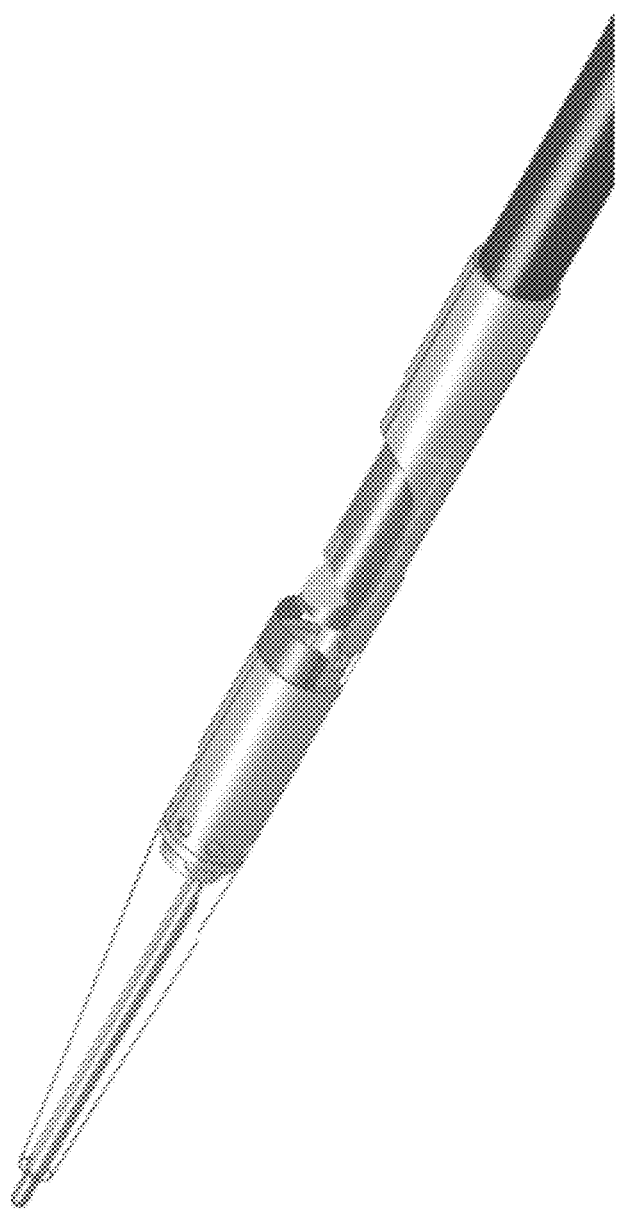
Figure 14A:
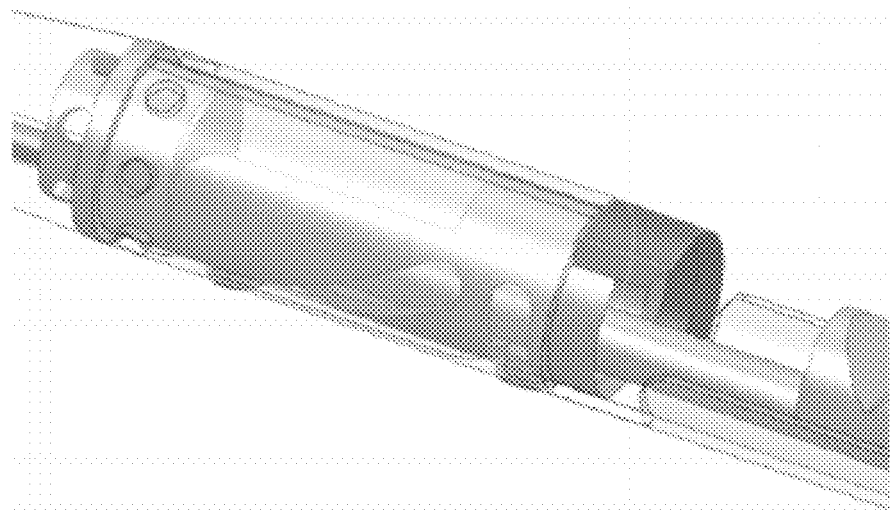
Figure 14B:
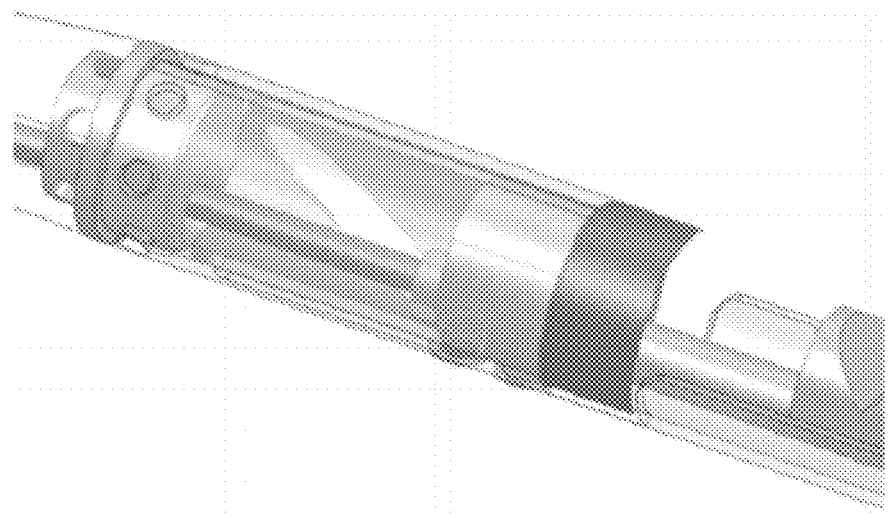
Figure 15B:
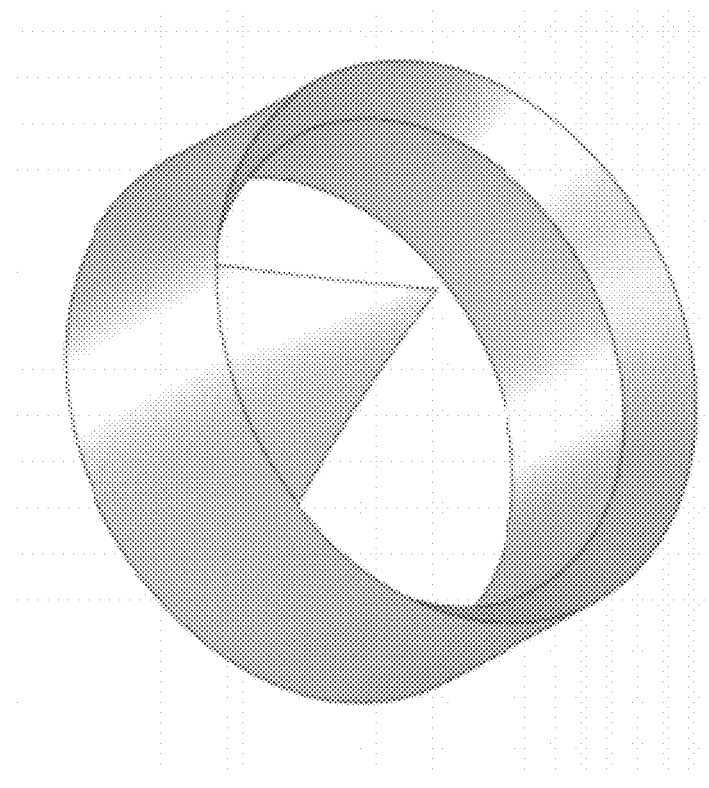
FIGS. 15A-15D illustrates exemplary cutters.
Figure 15A:
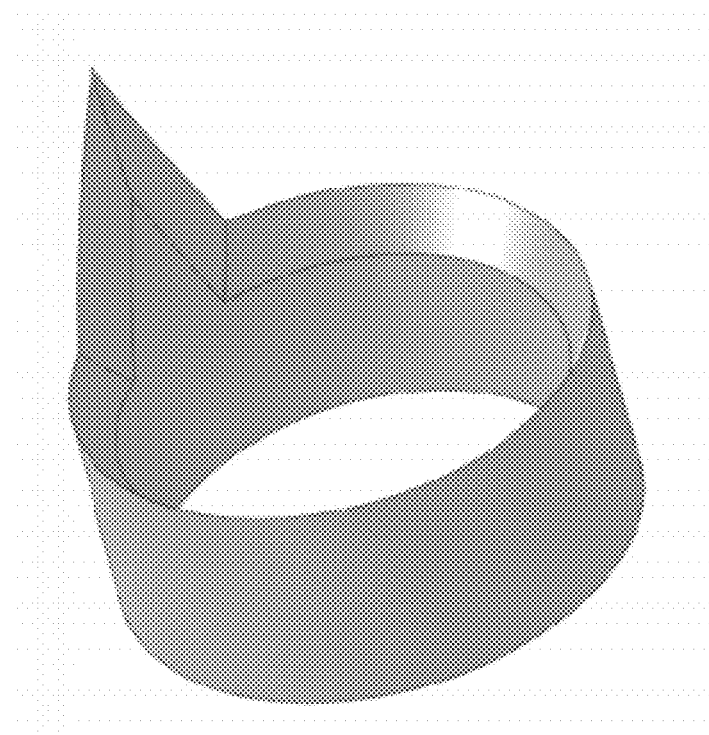
Figure 15D:
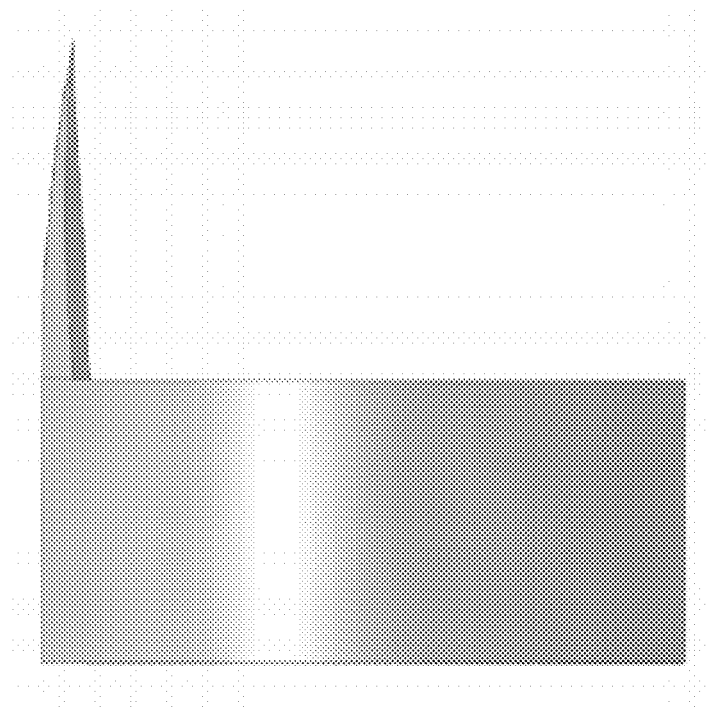
Figure 15C:
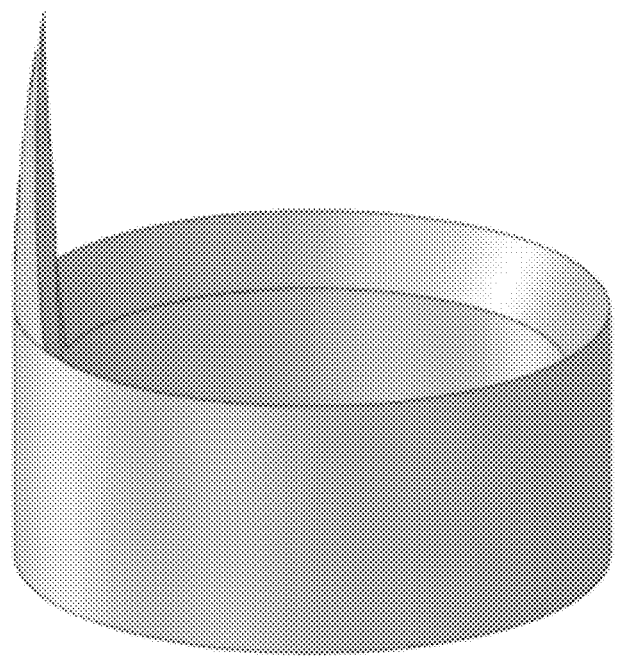

FIGS. 9A and 10 show one variation of a handle 901 for controlling the catheters described herein. FIG. 9A shows a system including an atherectomy catheter 900 connected to a handle 901; a second handle 904 is also shown attached. This second handle (shown in greater detail in FIG. 9B) may be used to help provide additional control of the atherectomy catheter. In some variations, the handle may be configured to be re-used with different atherectomy catheters. For example, the proximal end of the catheter may include connectors or adapters to mate with connectors in the handle to enable the various drive shafts to be controlled. In some variations, the handle is integrally connected to the proximal end of the catheter.

The handle shown in FIG. 9A is configured to separately control the cutting drive shaft and the imaging drive shaft. One or more controls 903 may be included to activate the cuter and/or the imaging. Alternatively, the handle may communicate with a controller (e.g., part of a visualization station) which may directly or remotely control the activation of the cutter and/or imaging sensor. Internal detail for the handle is shown in greater detail in FIG. 10, in which an outer cover from the handle of FIG. 9A has been removed. In FIG. 10, two separate drivers for the imaging and cutting drive shaft s are included within the handle. The handle also houses gearing that allows the imaging drive shaft to change direction (between clockwise and counterclockwise) in an automatic, continuous manner.

Also described herein, and shown in FIGS. 9A and 9B, is a torque or control handle 904, which may be slid and locked into position on the elongate length of the catheter. This control handle may be locked onto the body of the catheter and may provide a grip to enhance comfort and control of the device, particularly when a substantial region of the length of the device remains outside of the body. In this example the control handle includes a control 905 (e.g., button, slider, etc.) for releasing and locking the handle onto various positions along the length of the catheter. The control handle may also include a separate control (e.g., button, etc.) for activating one or more functions otherwise controlled by the handle, such as starting/stopping rotating of the cutter and/or imaging sensor, etc. Thus, in some variations the control handle may be in communication (including wired or wirelessly) with the proximal handle including the rotational actuators.

The handle 1001 shown in FIG. 10 is one variation of a handle for a catheter having a separate drive shaft for the cutter (cutter drive shaft 1030) and the imaging sensor (imaging drive shaft). In this example, the inner drive shaft 1030 controls the cutter, which is rotated by a motor 1033. This inner drive shaft may also be pushed distally and pulled proximally to deflect the distal tip; thus the gears for rotating the drive shaft allow a portion of the controller 1040 to shift axially distally or proximally. A second actuator (motor 1043) may be used to drive this lateral motion. Thus rotation of the actuator is translated into axial/distal motion along the threaded screw 1044 on which the controller 1040 rides.

The side view of the handle shown in FIG. 10 includes a housing that has been made transparent (e.g., or for which an outer cover has been removed) to visualize the internal components of the handle 1001. In this example, the catheter extends from the distal end. The device may also include cords such as power and optic/imaging cords (not shown) coupled to the handle. The optical fiber (not visible) may be held within a channel 1057 and directed to the optical outputs for image processing. In the variations shown, the optical fiber may be secured in handle and held (e.g., affixed) relative to the handle, as previously mentioned. Thus, the proximal end does not typically rotate, but is fixed relative to the handle. The handle body may be covered by a housing which may be configured to conform to a hand or may be configured to lock into a holder (e.g., for connection to a positioning arm, a bed or gurney, etc.

The imaging drive sub-system within the handle 1001 may include a motor 1003 and drive gears 1015, 1016, 1017 that can drive the imaging drive shaft to rotate the imaging sensor on the rotatable chassis at the distal end of the device allowing OCT imaging into the walls of the vessel, as described above. In some variations the imaging drive sub-system is controlled or regulated by a toggling/directional control subsystem for switching the direction of rotation of the drive shaft between the clockwise and counterclockwise direction for a predetermined number of turns (e.g., between about 4 and about 100, e.g., between 8 and 20, about 10, etc.). In FIG. 10, one variation of a directional control is a mechanical directional control, which mechanically switches the direction of rotation between clockwise and counterclockwise when the pre-determined number of rotations has been completed. In this example, the directional control includes a threaded track (or screw) 1011 which rotates to drive a nut 1013 in linear motion; rotation of the threaded track by the motor 1003 results in linear motion of the nut along the rotating (but longitudinally fixed) threaded track 1011. As the motor rotates in a first rotational direction (e.g., clockwise), the nut 1013 moves linearly in a first linear direction (e.g., forward) until it hits one arm of a U-shaped toggle switch 1016, driving the U-shaped toggle switch in the first linear direction and flipping a switch to change the direction of the motor 1003 to a second rotational direction (e.g., counterclockwise), and causing the nut to move linearly in a second linear direction (e.g., backward) until it hits the opposite side of the U-shape toggle switch 1016, triggering the switch to again change the direction of the motor back to the first rotational direction (e.g., clockwise). This process may be repeated continuously as the motor is rotated. The motor may be configured to rotate in either direction at a constant speed. The system may also include additional elements (e.g., signal conditioners, electrical control elements, etc.) to regulate the motor as it switches direction.

The number of threads and/or length of the threaded track (screw) 1011 may determine the number of rotations that are made by the system between changes in rotational direction. For example the number of rotations may be adjusted by changing the width of the shaped toggle 1014 (e.g., the spacing between the arms); lengthening the arms (or increasing the pitch of the screw) would increase the number of rotational turns between changes in direction (n). The toggle may therefore slide from side-to-side in order to switch the direction of the motor.

In some variations the motor is rotated in a constant direction and the switch between clockwise and counterclockwise are achieved by switching between gearing systems, engaging and disengaging an additional gear or gears that mechanically change the direction that the driveshaft is driven.

As mentioned above, the catheters described herein typically an elongate, flexible catheter length extending from the handle. The catheter typically includes an outer sheath surrounding an inner guidewire lumen (not shown). The various drive shafts extend along the length of the catheter to drive the cutter and/or imaging sensor at the distal end of the device in rotation. In some variations the imaging drive shaft is a tubular shaft and may surround the cutter drive shaft. The cutter drive shaft may be a solid shaft which extends through the length of the catheter.

In the exemplary device shown in FIG. 10, the imaging drive sub-system includes the motor 1003 and three gears 1017, 1016, 1015 that engage each other to drive the drive shaft in rotation. For example, the motor 1003 rotates a first gear 1017 which is engaged with a second gear 1016 (shown in this example as a 1:1 gearing, although any other gear ratio may be used, as appropriate). A third gear 1015 engages with the second gear 1016; the third gear may drive or regulate an encoder 1007 for encoding the rotational motion. This encoded information may in turn be used by the drive system, providing feedback to the drive system, or may be provided to the imaging system as discussed briefly below.

In operation, the user may turn on a switch (e.g., on the handle and/or the torque/control handle) to start operation of the overall system, including the rotation of the imaging system and/or cutter. In some variations the user may control the rate or speed of operation by controlling these rates of rotation, as mentioned above.

In any of the variations shown herein, the distal end of the catheter may include one or more fiduciary marks to aid in visualizing the catheter or to help determine the catheter orientation relative to the patient. For example, the catheter may include one or more electodense regions or markers that can be readily visualized using fluoroscopy to help orient the device within the body, including the rotational orientation. Any of the systems described herein may also include a control system for receiving and displaying the images received from the imaging sensor. The control system (e.g., see U.S. patent application Ser. No. 12/829,267 and U.S. patent application Ser. No. 12/790,703) may connect to the handle and control or modify the rotation rate, rotation direction, cutting speed, contrast, display, data storage, data analysis, etc. of the atherectomy device.

Additional Examples

FIGS. 11-14B illustrate one variation of an atherectomy catheter having a cutting element (shown in this example as a semi-circular cutting element) that is actuated by longitudinal displacement of a drive mechanism. The drive mechanism may be a shaft, as mentioned above.

The variation illustrated in FIGS. 11-14B are configured as pull-to-cut atherectomy catheters, in which tissue may be collected in the distal nose region. Alternatively, in some variations the device may be configured as push-to-cut catheters. A tissue packing plunger may also be used to secure tissue within the collection region, and/or to cover the cutting element when not in use. It should be noted that either collection in the distal or proximal regions of the catheter may be used in pushing or pulling configurations, as the tissue may be channeled or deflected into the collection region of the device.

FIGS. 15A-15D illustrate variations of cutting elements that may be used. Because the cutter is driven in an oscillatory motion, the cutter edge can be configured for optimal cutting efficiency and is not limited to circular edges with continuously rotating cutters.

Figure 16:
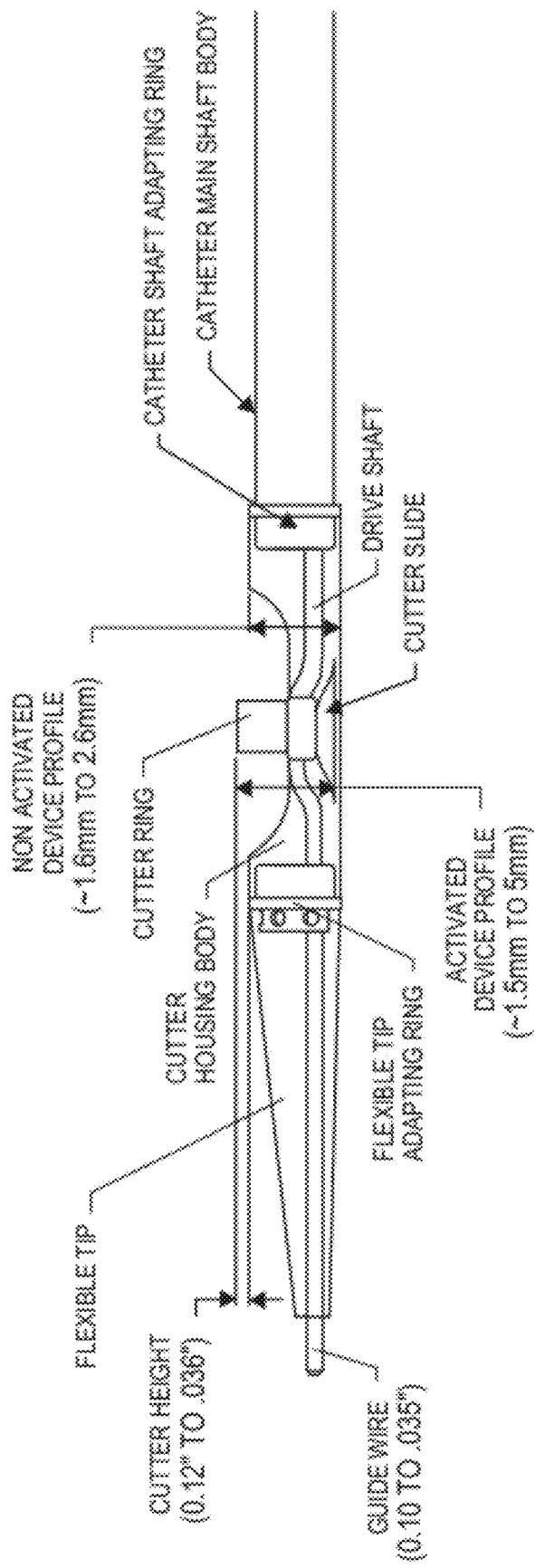
FIGS. 16-18 illustrate another variation of an atherectomy catheter having a cutting element.
Figure 17A:
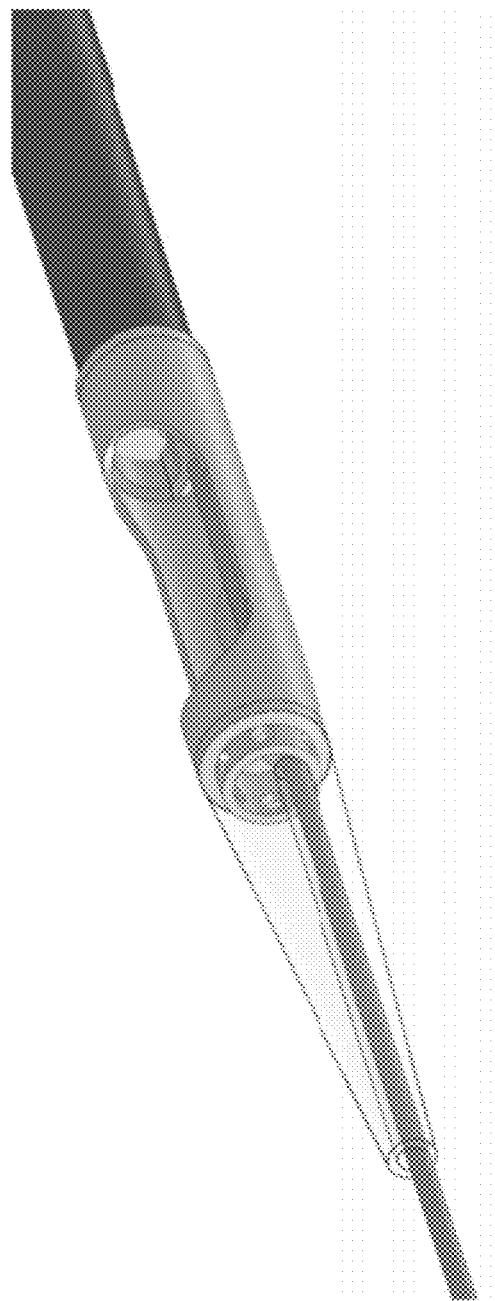
Figure 17B:
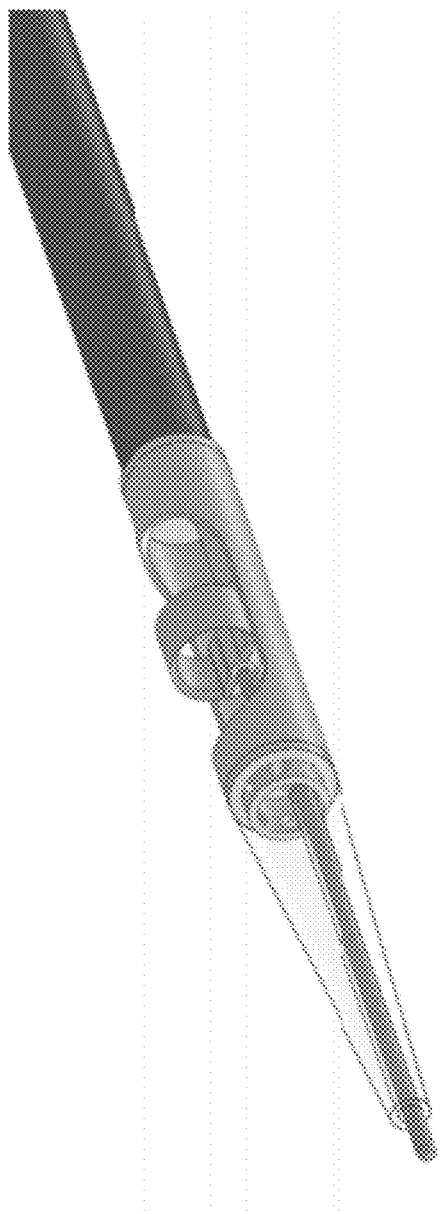
Figure 17C:
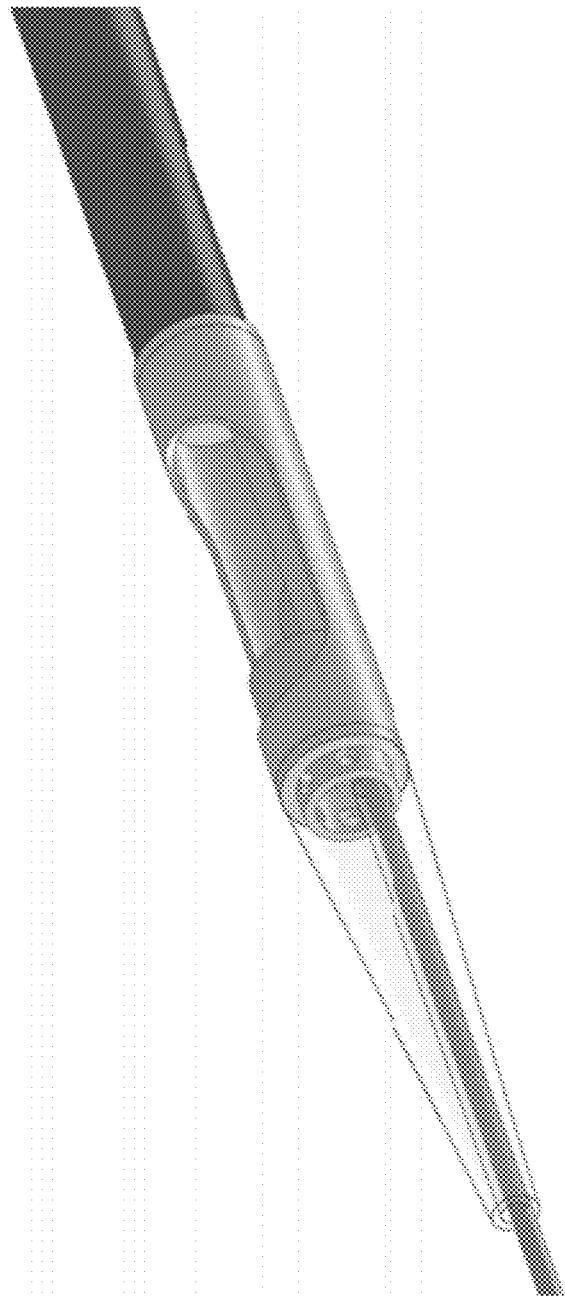
Figure 18:
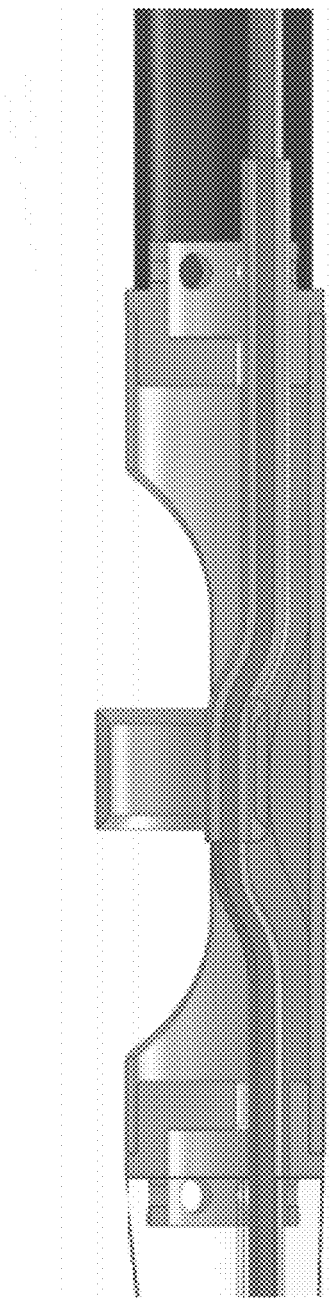

FIGS. 16-18 and illustrate another variation of an atherectomy device having a longitudinally actuated cutter. This variation is configured to cut as the blade slides both back and forth across the opening. In some variations tissue is not collected within the catheter, but is collected downstream in the vessel by a second or auxiliary device.

In any of these variations, the catheter device may also include on-board and real time image guidance capabilities. This may include an imaging element, or energy emitting assembly, positioned at the distal portion of the device such that local images of the vessel may guide device usage. One specific configuration of an OCT system that may be used for this distal imaging element is described in co-pending applications, including U.S. patent application Ser. No. 12/790,703, previously incorporated by reference. The distal energy emitter(s) may be positioned in multiple locations in fixed positions or embodied in a mating assembly that may translate in an eccentric lumen or in the hollow lumen of the driveshaft. The emitter may send and receive relevant light or sound signals at 90 degrees from the catheter axis or at angles up to approximately 50 degrees to visualize distal or proximal wall features from a fixed position.

Furthermore, the data collected at the distal end of the catheter, after transmitted and appropriately processed, may drive an automated means of tip actuation and cutter position. Increased amounts of disease detected by the software may automatically increase tip axially offset consequently increasing cut depth and apposition force. Cutter speeds, gear ratios and torque inputs may be adjusted according to input from the imaging system.

As mentioned brie fly above, in some variations any of the atherectomy catheters may be configured for use, and used, without a rotating imaging system (e.g., OCT imaging system). Alternatively, in some variations, such as those shown in FIGS. 21A and 21B, the imaging sensor is controlled on-axis.

FIGS. 21A-B illustrate an additional variation of the atherectomy catheter similar to those described above in FIGS. 1-7B, in which the imaging sensor is rotated with the cutter. In this variation, the second drive shaft (imaging drive shaft) is not included, and the imaging sensor may be affixed to a rotating chassis that is also rotated by the same drive shaft driving the cutter. In some variations the imaging sensor is rotated at the same rate as the cutter; in other variation (not illustrated in FIGS. 21A-B) there is a gearing between the drive shaft for the cutter and the rotatable imaging chassis so that the rate of rotation of the imaging sensor is geared to step down from the rate of the cutter rotation.

For example, FIG. 21A shows a portion of an atherectomy device having an imaging sensor that is rotated by the cutter drive shaft just proximal to the distal end of the catheter. This region includes the cutter 2104 and imaging sensor 2117. In this variation, the imaging sensor includes a mirror so that the fiber optic is configured to "look" at the walls of the vessel in which the atherectomy device is positioned. The device typically operates as described above; the distal tip region (not shown) may be displaced to expose the cutter 2104, and cut may be rotated to cut the tissue. Tissue that is cut may be stored in the distal tip region.

FIG. 21B shows one variation of the cutter and imaging catheter in which the two are coupled together so that rotation of the cutter also rotates the imaging catheter. A cutter drive shaft 2108 drives rotation of both the cutter 2014, via a cutter shaft 2114, spacing it from the imaging sensor 2117. The imaging sensor 2117 is affixed a rotatable chassis 2119, in this variation, the optical fiber 2110 is secured within a channel within the chassis to position the optical fiber in the central lumen region of the catheter (e.g., within the drive shaft 2108). During rotation, the chassis 2119 rotates with the cutter, rotating the distal end of the optical fiber, and allowing imaging during rotation; the optical fiber within the center of the catheter is allowed to freely rotate, although it may be constrained within a channel in the lumen of the drive shaft by the diameter of this channel. As it rotates in a first direction (e.g., clockwise), the optical fiber may be twisted upon itself. Although this would seem counterintuitive, the centered fiber may robustly handle hundreds of rotations without damage. After a predetermined number of rotations (e.g., 200, 300, 400, 500, 600, 700, 800, 900, 1000, 1500, etc.), the drive shaft may switch the direction of rotation and my continuously toggle back and forth between these directions as previously described. Thus, the cutter may also change direction.

Imaging Catheters

Also described herein are imaging catheters that do not necessarily including cutting elements as described above. For example, in some variations an imaging catheter may include an elongate body having a distal end that includes an imaging sensor (e.g., an OCT imaging sensor) including fiber optic element that is attached to the distal and extends (loose or unattached) within the elongate body of the catheter until it is secured in a proximal end of the device. In some variations just the distal tip of the imaging catheter is configured to rotate with the imaging sensor; in some variations the entire imaging catheter outer body may rotate, including the imaging sensor. In general, the imaging catheters described herein allow the optical fiber to be wound, wrapped or coiled as the imaging sensor is rotated. Thus, the distal and proximal ends may be fixed; for example, the distal end may be fixed to a rotatable chassis that may rotate relative to the handle, while the proximal end of the fiber is fixed relative to the rotating distal tip, and the intermediate portion is allowed to wrap and/or twist while in rotation. As a result, the imaging sensors are configured to rotate for a finite number of rotations in a first (e.g., clockwise) direction, followed by rotation in the opposite (e.g., counterclockwise) direction, and this clockwise/counterclockwise rotation may be repeated.

As mentioned above, the devices described herein may be rotated through a surprising number of rotations without damaging the fiber optic properties; in some variations in which the optical fiber is allowed to twist around itself (rather than wrapping around a shaft, wire, or the like) the fiber may be rotated for hundreds or rotations (e.g., 100, 200, 300, 400, 500, 600, etc.). The optical fiber may be held within a channel or passage having a fixed diameter to prevent the twisting fiber from kinking. In some variations, the optical fiber may be coated or clad with a material to provide support or strength; for example, the optical fiber may be coated with an elastomeric material, or a stiffer material.

For example, FIGS. 19A-20 illustrate two variations of imaging catheters in which the optical fiber is allowed to coil or wind up as the device is operated, e.g., as the imaging sensor is rotated at the distal end of the catheter. In both variations the imaging sensor is configured as an OCT imaging sensor formed of an optical fiber that affixed (e.g., embedded in an epoxy) so as to image within or through the lumen of a vessel. The imaging sensor in these examples may include a mirror for directing the imaging light out of the catheter and into the walls of the lumen; thus the imaging sensor may be configured to image to the side (e.g., approximately 90° off the long axis of the catheter), forward, backward, or some variation in between. The distal end of the optical fiber forming the imaging sensor is typically secured to a rotating element, at or near the tip. The proximal end of the optical fiber may also be fixed, and does not rotate relative to the distal end of the device. The portion of the fiber extending between the proximal and distal ends is typically free to rotate and, in some variations, wind or unwind within a lumen and/or around a wire or shaft within the catheter.

The imaging catheter 1900 shown in FIG. 19A includes an outer sheath (torque shaft 1907) that remains stationary while distal end region (imaging window 1903) rotates; the distal end of the optical fiber 1903 is affixed to the rotating imaging window 1903, which may be configured as a rotatable chassis. This chassis may be rotated by turning the central wire that is configured as a drive shaft 1905. As the drive shaft is rotated and rotates the imaging window 1915, the imaging sensor sweeps a beam of light 1912 around the perimeter. The drive shaft (wire) may be any appropriate material, including braided, solid, or hollow materials; in some variations the drive shaft is Nitinol. The distal tip region 1913 may be configured to prevent damage to tissue. For example, the distal tip region may be soft and rounded (atraumatic). Thus, in this variation the drive shaft 1095 rotates (spinning the distal end region 1915) while the torque shaft 1907 remains stationary, allowing the fiber optic to wrap around the torque shaft. In one exemplary variation the outer diameter of the shaft is approximately 0.0335 inches, the length is approximately 57 inches, and the diameter of the drive shaft (wire) is approximately 0.011 inches.

In operation, this imaging catheter may be used as an OCT imaging catheter, and allowed to rotate the drive shaft (and thus the imaging sensor) alternately clockwise, then counter-clockwise some number of rotations. The number of rotations clockwise/counterclockwise may be predetermined, or it may be based on some estimate of tension in the optical fiber.

FIG. 19B shows a variation of an imaging catheter similar to the variation shown in FIG. 19A, however the rotating imaging window region 1915 includes a one or more openings 1909 to allow "flushing" of the imaging sensor. Flushing may help clear the imaging sensor from blood and other debris that may otherwise prevent clear imaging. In some variations the imaging sensor is flushed by applying pressurized fluid (e.g., saline, etc.) through the catheter body as described above.

Another variation of an imaging catheter is shown in FIG. 20. In this example, the imaging catheter includes an outer torque shaft 2003 that rotates, while the fiber optic 2001 twists on itself within the lumen of the catheter. In this variation the distal end of the optical fiber is secured to the imaging window region 2005 of the catheter. This distal tip region 2005 rotates as the torque shaft 2003 rotates, rotating the distal end region of the optical fiber. In any of the variations described herein, the distal end of the optical fiber may be secured by epoxy or other appropriate means (e.g., to a rotatable chassis, catheter tip, etc.); for example, the end of the fiber optic may be encapsulated in an epoxy at the distal end of the device by a material 2010 having an appropriate index of refraction (e.g., see U.S. patent application Ser. No. 12/790,703, titled "OPTICAL COHERENCE TOMOGRAPHY FOR BIOLOGICAL IMAGING" and filed on May 28, 2010). Thus, the end of the fiber optic may be formed as part of a beam-tuning region 2013 for emitting/receiving the beam into/from the tissue and forming the OCT image from the tip 1005 region of the catheter. In one exemplary variation, the catheter (torque shaft) has an outer diameter of approximately 0.0375 inches (0.0340 inches in another example) and a length of approximately 54 inches (55 inches in another example), however, any appropriate dimensions may be used.

Additional details pertinent to the present invention, including materials and manufacturing techniques, may be employed as within the level of those with skill in the relevant art. The same may hold true with respect to method-based aspects of the invention in terms of additional acts commonly or logically employed. Also, it is contemplated that any optional feature of the inventive variations described may be set forth and claimed independently, or in combination with any one or more of the features described herein. Likewise, reference to a singular item, includes the possibility that there are plural of the same items present. More specifically, as used herein and in the appended claims, the singular forms "a," "and," "said," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise herein, all technical and scientific terms used herein have the same meaning as commonly understood by one of ordinary skill in the art to which this invention belongs. The breadth of the present invention is not to be limited by the subject specification, but rather only by the plain meaning of the claim terms employed.

We claim:

1. An atherectomy catheter device configured to visualize and to cut tissue, the device comprising:
    an elongate catheter body;
    a distal tip attached to the elongate catheter body;
    a cutter having a distal cutting edge, the cutter configured to rotate relative to the elongate catheter body;
    a cutter drive shaft within the elongate catheter body and connected to the cutter, the cutter drive shaft configured to rotate the cutter, wherein the cutter drive shaft is further configured to be longitudinally displaced proximally or distally to deflect the distal tip to expose the cutting edge of the cutter; and
    an optical fiber within the cutter drive shaft extending a length of the elongate catheter body, a distal end of the optical fiber forming an imaging sensor;
    wherein the distal end of the optical fiber is rotationally fixed to the cutter and configured to rotate therewith during imaging, a proximal end of the optical fiber is rotationally fixed to a portion of the catheter device, and an area between the proximal end of the optical fiber and the distal end of the optical fiber is free to rotate within the cutter drive shaft.

2. The device of claim 1, further comprising a ramped slide surface between the distal tip and a region within the elongate body proximal to the cutter, wherein the ramped slide surface is configured to guide deflection of the distal tip as the cutter drive shaft is moved longitudinally.

3. The device of claim 1, wherein the imaging sensor comprises an OCT imaging sensor.

4. The device of claim 1, wherein the cutter comprises a ring cutter.

5. The device of claim 1, wherein the distal tip is configured to collect tissue cut by the cutter.

6. The device of claim 1, further comprising a proximal handle having a first driver for driving rotation of the cutter and a second driver for driving rotation of the imaging sensor.

7. The device of claim 1, further comprising a proximal handle having a first driver for driving rotation of the cutter between 100 and 4000 rpm, and a second driver for driving rotation of the imaging sensor at less than 100 rpm.

8. The device of claim 1, further comprising a proximal handle having a first driver for driving rotation of the cutter in a first direction and a second driver for alternately driving rotation of the imaging sensor in a first rotational direction and a second rotational direction.

9. The device of claim 1, wherein the portion of the catheter device is the handle.

10. The device of claim 1, wherein the cutter drive shaft is configured to be moved longitudinally to pack tissue into the distal tip.

11. The device of claim 1, wherein the area of the optical fiber between the proximal end and the distal end is not fixed to any portion of the device.

* * * * *